(12) United States Patent
Yee et al.

(10) Patent No.: US 12,256,642 B2
(45) Date of Patent: Mar. 18, 2025

(54) ULTRASOUND TRANSDUCER WITH DISTRIBUTED CANTILEVERS

(71) Applicant: Robert Bosch GmbH, Stuttgart (DE)

(72) Inventors: Seow Yuen Yee, Mountain View, CA (US); Vladimir Petkov, San Jose, CA (US); Matthias Boecker, Reutlingen (DE); Timo Schary, Aichtal (DE); Reinhold Roedel, Reutlingen (DE)

(73) Assignee: Robert Bosch GmbH (DE)

( * ) Notice: Subject to any disclaimer, the term of this patent is extended or adjusted under 35 U.S.C. 154(b) by 888 days.

(21) Appl. No.: 17/373,271

(22) Filed: Jul. 12, 2021

(65) Prior Publication Data
US 2023/0009789 A1    Jan. 12, 2023

(51) Int. Cl.
| | | |
|---|---|---|
| *H01L 41/113* | (2006.01) | |
| *B06B 1/06* | (2006.01) | |
| *G01B 17/02* | (2006.01) | |
| *G01S 7/521* | (2006.01) | |
| *G01S 15/931* | (2020.01) | |
| *H10N 30/30* | (2023.01) | |

(Continued)

(52) U.S. Cl.
CPC ......... *H10N 30/306* (2023.02); *B06B 1/0607* (2013.01); *G01B 17/02* (2013.01); *G01S 7/521* (2013.01); *G01S 15/931* (2013.01); *H10N 30/302* (2023.02); *H10N 30/50* (2023.02); *A61B 8/4483* (2013.01); *G01S 2015/932* (2013.01)

(58) Field of Classification Search
CPC ..... H10N 30/306; H10N 30/50; B06B 1/0607
See application file for complete search history.

(56) References Cited

U.S. PATENT DOCUMENTS

| | | |
|---|---|---|
| 6,310,831 B1 | 10/2001 | Dillman |
| 7,728,487 B2 | 6/2010 | Adachi et al. |

(Continued)

FOREIGN PATENT DOCUMENTS

| | | |
|---|---|---|
| CN | 110508474 A | 11/2019 |
| CN | 110518114 A | 11/2019 |

(Continued)

OTHER PUBLICATIONS

Karaman et al., "Minimally Redundant 2-D Array Designs for 3-D Medical Ultrasound Imaging," IEEE Trans. on Medical Imaging, vol. 28, No. July, pp. 1051-1061, 2009.

(Continued)

*Primary Examiner* — Bryan P Gordon
(74) *Attorney, Agent, or Firm* — Dickinson Wright PLLC

(57) ABSTRACT

An ultrasound transducer of a vehicle system includes a support member that attaches to and connects to the bottom portion of a membrane of the ultrasound transducer and supports the membrane, wherein the support member includes one or more cantilevers with a first end attaching to the membrane and a second end attaching to a support portion of the support member that attaches to the substrate, wherein the cantilever extends across and floats above the substrate, wherein the first end of the cantilever includes a stub extending away from a surface of the cantilever, wherein the stub extends away from the surface without contacting the substrate, wherein the one or more cantilevers includes one or more piezoelectric layers on the surface of the cantilever.

13 Claims, 27 Drawing Sheets

(51) Int. Cl.
*H10N 30/50* (2023.01)
*A61B 8/00* (2006.01)

(56) References Cited

U.S. PATENT DOCUMENTS

| | | |
|---|---|---|
| 7,982,362 B2 | 7/2011 | Adachi et al. |
| 8,324,006 B1 | 12/2012 | Adler |
| 8,345,513 B2 | 1/2013 | Huang |
| 8,421,170 B2 | 4/2013 | Bayram |
| 8,563,345 B2 | 10/2013 | Adler |
| 8,687,466 B2 | 4/2014 | Kim |
| 8,852,103 B2 | 10/2014 | Rothberg |
| 9,319,800 B2 | 4/2016 | Hong |
| 9,515,580 B2 | 12/2016 | Pinkerton |
| 9,571,008 B2 | 2/2017 | Milligan |
| 9,896,107 B1 | 2/2018 | Huang |
| 9,945,818 B2 | 4/2018 | Ganti |
| 10,186,654 B2 | 1/2019 | Bevilacqua et al. |
| 10,478,858 B2 | 11/2019 | Lasiter |
| 10,576,500 B2 | 3/2020 | Foncellino et al. |
| 10,656,255 B2 | 5/2020 | Ng et al. |
| 10,698,094 B2 | 6/2020 | Rudoy |
| 11,154,906 B2 | 10/2021 | Garlepp et al. |
| 11,292,030 B2 | 4/2022 | Horsley et al. |
| 2001/0035700 A1 | 11/2001 | Percin et al. |
| 2005/0022585 A1 | 2/2005 | Berkman |
| 2006/0186762 A1* | 8/2006 | Sugiura ............ H03H 3/02 310/334 |
| 2007/0144261 A1 | 6/2007 | Okuda et al. |
| 2009/0001853 A1 | 1/2009 | Adachi et al. |
| 2009/0059726 A1 | 3/2009 | Okuda |
| 2009/0078023 A1* | 3/2009 | Mutharasan ....... G01N 33/5438 73/1.03 |
| 2010/0013574 A1 | 1/2010 | Huang |
| 2010/0277040 A1 | 11/2010 | Klee et al. |
| 2011/0051985 A1* | 3/2011 | Hwang ............ H04R 17/00 381/396 |
| 2011/0126625 A1 | 6/2011 | Mizota et al. |
| 2012/0269031 A1* | 10/2012 | Huffman ............ G01N 29/245 73/632 |
| 2015/0165479 A1* | 6/2015 | Lasiter ............ B06B 1/0666 29/25.35 |
| 2016/0027424 A1 | 1/2016 | Shimizu et al. |
| 2016/0339476 A1 | 11/2016 | Joyce et al. |
| 2017/0291545 A1 | 10/2017 | Lai et al. |
| 2019/0204428 A1 | 7/2019 | Harada et al. |
| 2019/0242985 A1 | 8/2019 | Ishii et al. |
| 2019/0293773 A1 | 9/2019 | Matsushita |
| 2019/0391263 A1 | 12/2019 | Ueda et al. |
| 2020/0030850 A1 | 1/2020 | Apte et al. |
| 2020/0049816 A1 | 2/2020 | Suzuki et al. |
| 2020/0137220 A1 | 4/2020 | Storbeck |
| 2020/0156114 A1 | 5/2020 | Gattere et al. |
| 2020/0256984 A1 | 8/2020 | Fukabori |
| 2020/0284890 A1 | 9/2020 | Ueda et al. |
| 2020/0288224 A1 | 9/2020 | Ueda et al. |
| 2020/0322730 A1 | 10/2020 | Kamiya et al. |
| 2020/0367858 A1 | 11/2020 | Baldasarre et al. |
| 2020/0412299 A1 | 12/2020 | Kurokawa et al. |
| 2021/0017016 A1 | 1/2021 | Anzinger et al. |
| 2021/0119105 A1 | 4/2021 | Seghizzi et al. |
| 2021/0154702 A1 | 5/2021 | Fujimoto et al. |
| 2021/0206625 A1* | 7/2021 | Paci ............ H10N 30/2047 |
| 2022/0040735 A1 | 2/2022 | Chang |
| 2022/0118480 A1 | 4/2022 | Giusti et al. |
| 2023/0011826 A1 | 1/2023 | Yee et al. |

FOREIGN PATENT DOCUMENTS

| | | |
|---|---|---|
| CN | 110523607 A | 12/2019 |
| DE | 102018106063 A1 | 9/2019 |
| EP | 3140869 B1 | 6/2019 |
| EP | 2478404 B1 | 3/2020 |
| EP | 3809476 A1 | 4/2021 |
| JP | 2021111957 A | 8/2021 |
| JP | 2021111964 A | 8/2021 |
| WO | 2016061410 A1 | 4/2016 |
| WO | 2021/079160 A1 | 4/2021 |

OTHER PUBLICATIONS

Hakobyan., "Orthogonal Frequency Division Multiplexing Multiple-Input Multiple-Output Automotive Radar with Novel Signal Processing Algorithms", Ph.D. Dissertation, University of Stuttgart, 2018, 191 Pages.

Zuniga et al., "Effect of a Central Antenna Element on the Directivity, Half-Power Beamwidth and Side-Lobe Level of Circular Antenna Arrays", in NASA/ESA Conference on Adaptive Hardware and Systems, 2009, pp. 252-256.

Akkaya., "Acoustic Radiation from Baffled Planar Sources: A Series Approach", Lubbock, TX: Master's Thesis, Texas Tech University, 1999, 134 Pages.

\* cited by examiner

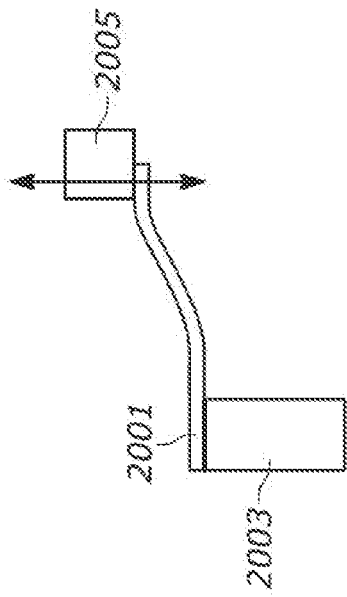 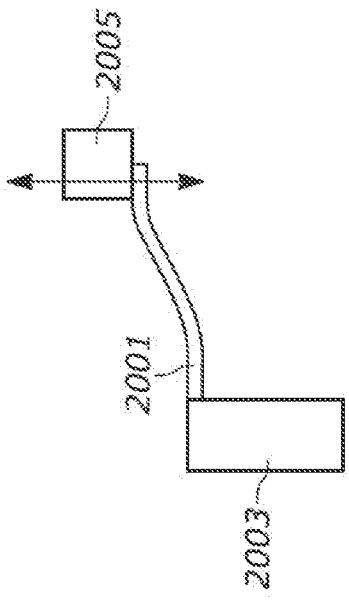
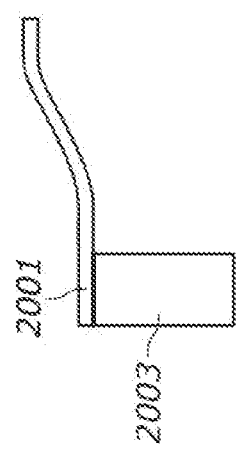 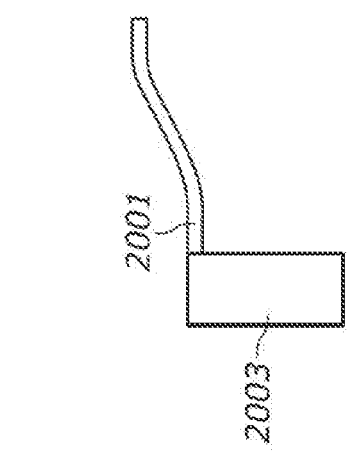
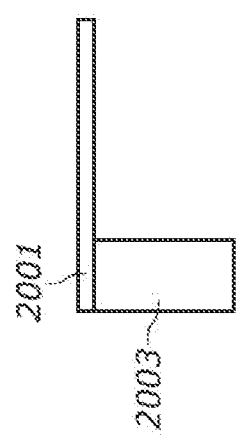

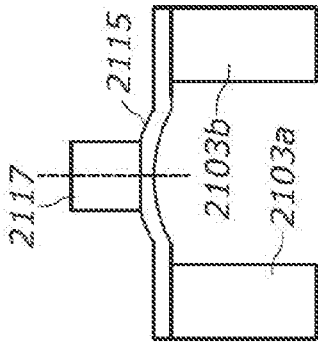
FIG. 21C
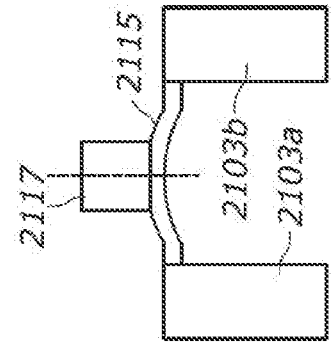
FIG. 21E
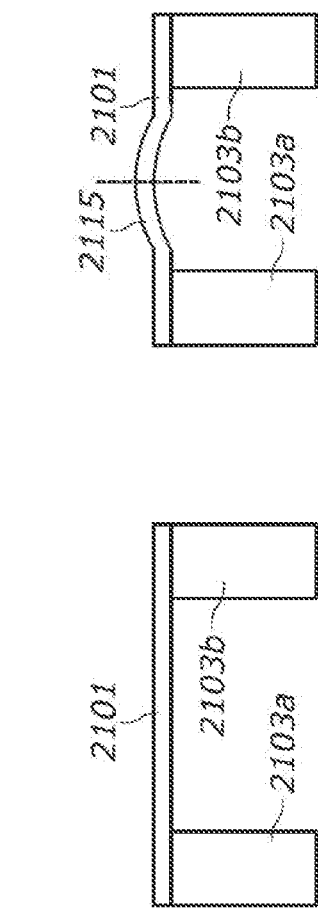
FIG. 21A
FIG. 21D
FIG. 21B
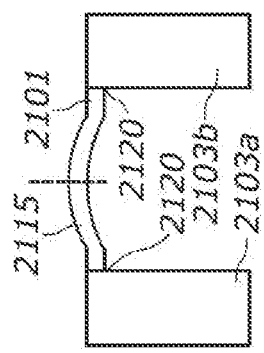
FIG. 21F
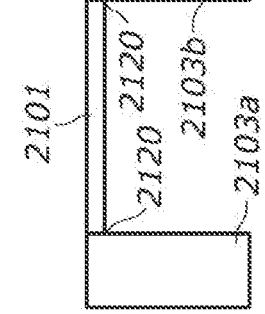

ULTRASOUND TRANSDUCER WITH DISTRIBUTED CANTILEVERS

TECHNICAL FIELD

The present disclosure relates to ultrasound sensors or other types of sensors, such as those utilized in parking assist systems.

BACKGROUND

Existing parking-assist systems may utilize ultrasound sensors (e.g., four to six bulk) mounted at distinct locations along one or each bumper of the vehicle. Each sensor may be implemented with a bending membrane, typically build out of aluminum, which transmits and receives acoustic pressure waves. The transmitted waves travel to a target object at a certain distance and after reflection arrive back at the membrane, where they generate a voltage signal. The voltage is detected by readout electronics and the time of flight is estimated, giving an estimate of the distance to the target.

SUMMARY

According to one embodiment, an ultrasound transducer of a vehicle system, wherein the ultrasound transducer includes a membrane including a top portion and a bottom portion, wherein the membrane is configured to vibrate and generate an ultrasound in response to voltage applied to one or more piezoelectric layers. The transducer also includes a support member that attaches to and connects to the membrane and supports the membrane, wherein the support member includes one or more cantilevers extending to and attaching to the membrane and a substrate, wherein a first end of the cantilever connects to the membrane and includes a stub, wherein the stub extends away from the cantilever, wherein the cantilever includes the one or more piezoelectric layers.

According to another embodiment, an ultrasound transducer of a vehicle system includes a support member that attaches to and connects to the bottom portion of a membrane of the ultrasound transducer and supports the membrane, wherein the support member includes one or more cantilevers with a first end attaching to the membrane and a second end attaching to a support portion of the support member that attaches to the substrate, wherein the one or more cantilevers extend across and floats above the substrate, wherein the first end of one of the cantilevers includes a stub extending away from a surface of the cantilever, wherein the stub extends away from the surface without contacting the substrate, wherein the one or more cantilevers includes one or more piezoelectric portions on the surface of the cantilever.

According to yet another embodiment, an ultrasound transducer of a vehicle system includes a membrane configured to vibrate to generate an ultrasound when voltage is applied and further configured to vibrate in an out-of-plane movement. The transducer includes a support member that attaches to and connects to the bottom portion of a membrane of the ultrasound transducer and supports the membrane, wherein the support member includes one or more platforms with a first end attaching to the membrane and a second end attaching to a support portion of the support member that attaches to the substrate, wherein the platform extends across and floats above the substrate, wherein the first end of the platform includes one or more stubs extending away from a surface of the platform, wherein the one or more stubs extend away from the surface without contacting the substrate, wherein the one or more platforms includes one or more piezoelectric layers on the surface of the platform.

BRIEF DESCRIPTION OF THE DRAWINGS

FIG. 20A-F discloses various embodiments of cantilevers with a fixed-guided end.

FIG. 21A-F discloses various embodiment of a bridge connected to a support structure.

DETAILED DESCRIPTION

Figure 1:
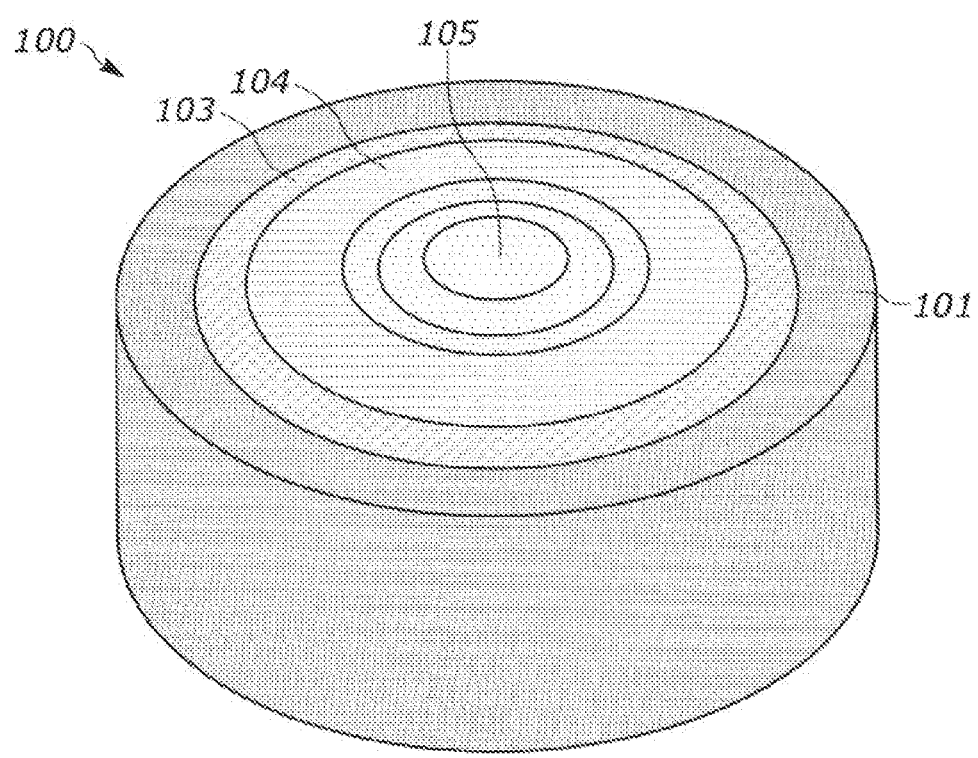
FIG. 1 is an illustrative embodiment of a transducer.

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

In order to create and/or detect oscillation or changes in resonance behavior, different kind of cantilever based structures, which are connected to an electronic or mechanical drive unit or element and a read out sensor element (e.g. AFM, gas detection, etc.) can be utilized. Cantilevers may be designed in at least two embodiments, a free-end cantilever or a fixed-guided cantilever. A point or distributed mass load can be attached to the end of the cantilever. If the distributed mass load is not perfectly stiff throughout on the fixed-guided cantilever, the cantilever may behave somewhere in between characteristics of the fixed-guided cantilever and the free-end cantilever. The frequency response characteristics of a fixed-guided cantilever with a distributed mass load may depend on the stiffness of this mass load as well as the placement of this mass load on the cantilever. During fabrication, it may be difficult to control the placement of the mass load on the cantilever, which may cause misalignment. The disclosure below shows different variations of embodiments that show misalignment, as well as compensating some of the flexibility in the distributed mass load. The bottom stub or double sided stubs may be utilized in one embodiment. In addition, various designs may be utilized that can incorporate a hard stop to limit the displacement beyond the fracture point.

This disclosure of the embodiments below describe an ultrasound sensor with enhanced functionality. The illustrative embodiments described below employ several independent piston-type transducers within the form factor of a single standard ultrasound sensor. The partitioning of the transducer area into independent elements allows for several improvements in the sensor function. In the embodiments below, the field of view can be changed dynamically, when a different number of elements is activated. The sensor may allow simultaneous transmission and reception from separate elements, thus improving the minimum detectable range. Furthermore, if the transducers are operated as a phased array, a beam steering function can be realized, allowing more targeted imaging.

FIG. 1 is an example of a first embodiment of a transducer 100. The transducer may include a support area 101 and membrane 105. The support area 101 may be a fixed support area with a membrane. When a transducer is exposed to harsh environments such as automotive, industrial, medical or other applications (such as micro-pumps where complete seal is needed), the transducer may need to withstand impact from high-velocity particles, provide a barrier for contamination, prevent exposure to moisture in the air which might freeze in cold weather, avoid exposure to harsh chemicals or fluids, withstand high pressure cleaning processes, and so on. For such applications, the choice of design is normally a continuous membrane of a certain thickness to withstand impact, or a more fragile membrane but with housing or packaging which can protect the membrane from harsh environments. However, the housing or packaging often creates signal or performance loss and is not desired. In addition, for continuous membranes with a certain thickness, the higher the thickness of the membrane, the better it can withstand impact but at the same time, it is also harder to deflect such membranes. Therefore, a novel way of transducer design is introduced in this invention record to address the harsh environment while achieving large signal or displacement of the membrane.

It may be important for vehicle applications of a park pilot transducer to be able to withstand such harsh environments, (e.g. mud, ice, hitting by stone), have a resonance frequency set to a specific parameter (e.g. 48 kHz), have a measurement range 5.5 m and a minimized cost of production. To achieve large measurement range, the transducer must be able to generate sufficient sound pressure level, which in turn means a membrane that can displace sufficient volume of air, and also to be sensitive to incoming waves, which have to be absorbed by the membrane in a way that notable mechanical oscillation results which have to be converted to an electrical output signal.

According to an embodiment, a bending mode of a membrane may be where all boundaries of the membrane 103, 104 are connected to fixed supports and only the center 105 of the membrane deflects (e.g., the center of the membrane 105 deflects the most while the support area 101 does not deflect). Thus, the boundaries 103, 104 of the membrane may produce less movement than the center 105 of the membrane itself. As the center 105 moves out-of-plane away from the support area 101, the other boundaries located closer to the support structure 101 may have less vibration than the center 105. For example, boundary 103 may have less out-of-plane movement than boundary 104.

Figure 2:
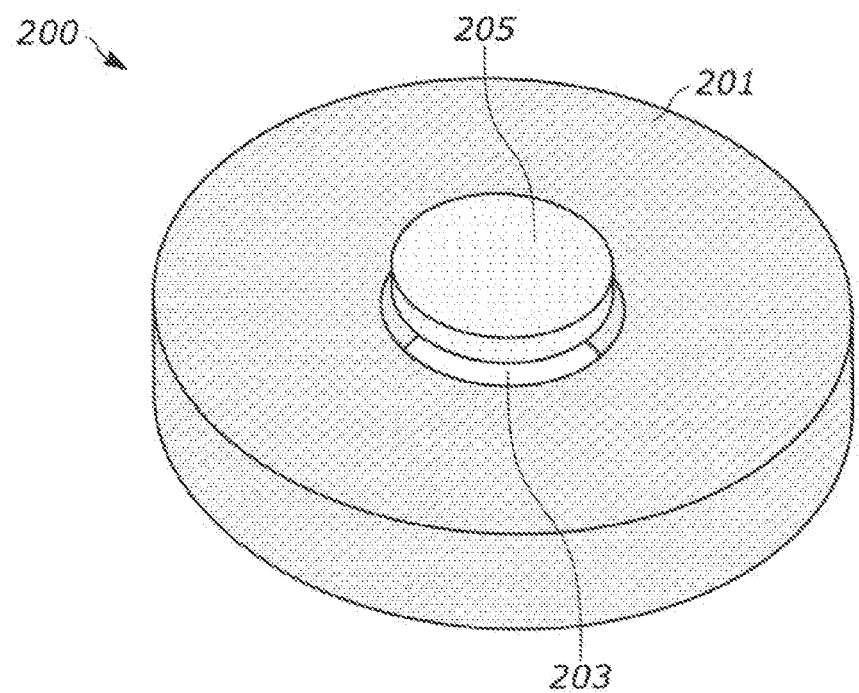
FIG. 2 is an illustrative embodiment of a transducer in a piston mode.

FIG. 2 is an example of a piston mode of a transducer. In the piston mode, all boundaries of the membrane are free to move and the membrane deflects in such a way where the whole surface is displaced equally. The fixed support area 201 may surround the center 205 of the membrane of the transducer 200. The center membrane 205 may be connected to the fixed support area 201 via a gasket 203 or seal 203. The fixed support area 201 may have no movement relative to the fixed support area 201, or very little out-of-plane movement. The transducer 200 may produce transmission of the ultrasound signal based on movement of the membrane 205. The more movement with respect to the membrane 205, the more power of the transmission of the ultrasound signal.

Figure 3A:
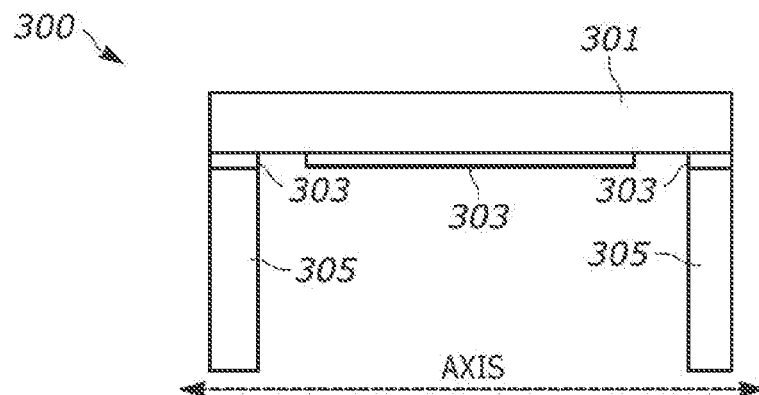
FIG. 3A is an example of a side view of a bending and piston mode in parallel.
Figure 3B:
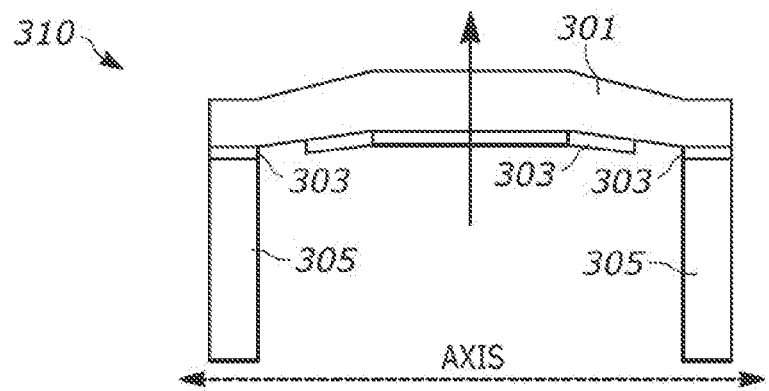
FIG. 3B is a bending mode when the transducer is actuated.
Figure 3C:
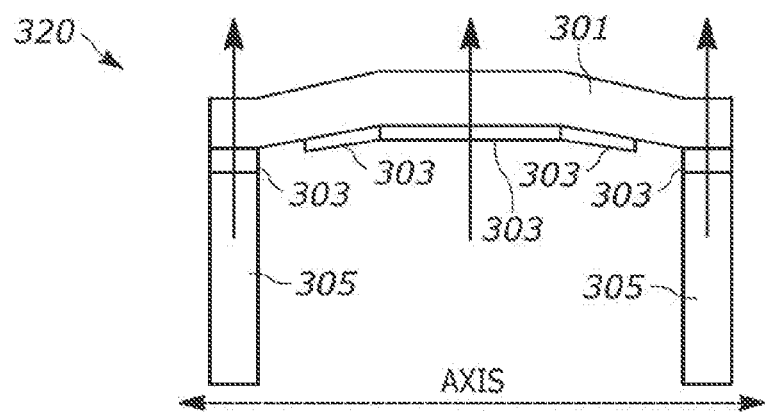
FIG. 3C illustrates a side view when both the bending mode and the piston mode of a transducer are actuated.

FIG. 3A is an example of a side view of a bending and piston mode in parallel. FIG. 3B is a side view of a bending mode when the transducer is actuated. FIG. 3C is a side view of a bending and piston mode both being actuated. There may be multiple ways to combine bending and piston modes for ultrasound transducers in many embodiments. In one embodiment, both the bending and piston modes act on the same membrane. In an alternative embodiment, a bending-mode cantilever or membrane translates the motion to a piston-mode membrane. Such embodiments may be responsive to how the fixed support and boundary conditions are determined. Although in some embodiments, piezoelectric (e.g. lead zirconate titanate (PZT)) actuation and sensing is described as an example, such an embodiment can be expanded to electrostatic actuation or capacitive sensing, as well as electromagnetic, etc. In one embodiment, the system may have a parallel connection of the bending mode and the piston mode.

Traditionally, for bending mode membranes, a piezoelectric layer may be placed at the center of the membrane where when voltage is applied, the piezoelectric layer may expand or shrink (e.g., known as inverse piezoelectric effect) in plane with the membrane while creating out of plane displacement on the membrane. The edges of the membrane may be bounded to a fixed support, limiting the movement of the edges. This bending mode may be most effective for flexible and thin membranes, which can achieve large displacement. Similarly, for sensing, the pressure on the membrane will cause deflection in the piezoelectric layer, converting mechanical energy to electrical energy (known as piezoelectric effect) and a voltage change is recorded. The more flexible the membrane, the larger the deflection and hence the higher the voltage change.

As shown in FIG. 3A, instead of fixed support on the edges of the membrane 301, the membrane 301 is connected to a support structure 305 allowing movement out of plane of the membrane 301 also on the outer edge and create higher displacement of the membrane than just the bending mode displacement. The membrane may include a piezoelectric layer 303, which may include a middle piezo layer 303 or outer piezo layer 303. The middle piezoelectric layer 303 may be located in the middle or center of the membrane 301. The outer piezoelectric layer 303 may be connecting the membrane 301 to the support structure 305. Thus, the piezoelectric layer may be a layer between the membrane 301 and the support structure 305, however, the transducer 300 may include a portion below the bottom surface of the membrane 301 that does not include a piezoelectric layer or a support structure. The piezo electric layer 303 may be utilized to generate electrical signals in response to various signals and actuations. The piezoelectric layer 303 may be in the center of the membrane and be concentric to the membrane. Furthermore a first piezoelectric layer may not touch or abut the second piezoelectric layer that is aligned with the outer edge of the membrane. The first and second piezoelectric layer may be axially aligned and parallel with each other. As shown in FIG. 3A, the top surface and bottom surface of the membrane are substantially parallel. Instead of fixed support on the edges of the membrane 301, the membrane 301 is connected to a support structure 305 allowing movement out of plane and create higher displacement of the membrane than just the bending mode displacement. In another embodiment, the middle piezoelectric layer 303 may be a ring with a hollow center and thus not be a solid disc.

FIG. 3B is a bending mode 310 when the transducer is actuated. In such an embodiment, the bending mode may only be actuated, and thus the piston mode is not actuated. The support structure 305 in such a scenario may be rigid and provide very little movement away from the top surface and bottom surface of the membrane 301. The support structure 305 may be silicon or any other material, allowing a first passive piston movement (not shown in illustration).

Thus, the center piezoelectric layer 303 may cause out-of-plane movement of the membrane 301 towards a center portion of the membrane.

FIG. 3C illustrates a side view when both the bending mode and the piston mode 320 of a transducer are actuated. As shown in the illustration, such a mode causes movement away from the top surface of the membrane 301 and out-of-plane movement from an axis running parallel and across the membrane. A portion of the membrane 301 axially away from a horizontal axis across both support structures may also cause movement away from the horizontal axis. As shown in FIG. 3C, movement away from the top surface of the membrane 301 is at each area of the membrane adjacent the piezoelectric layer 303.

Figure 4:
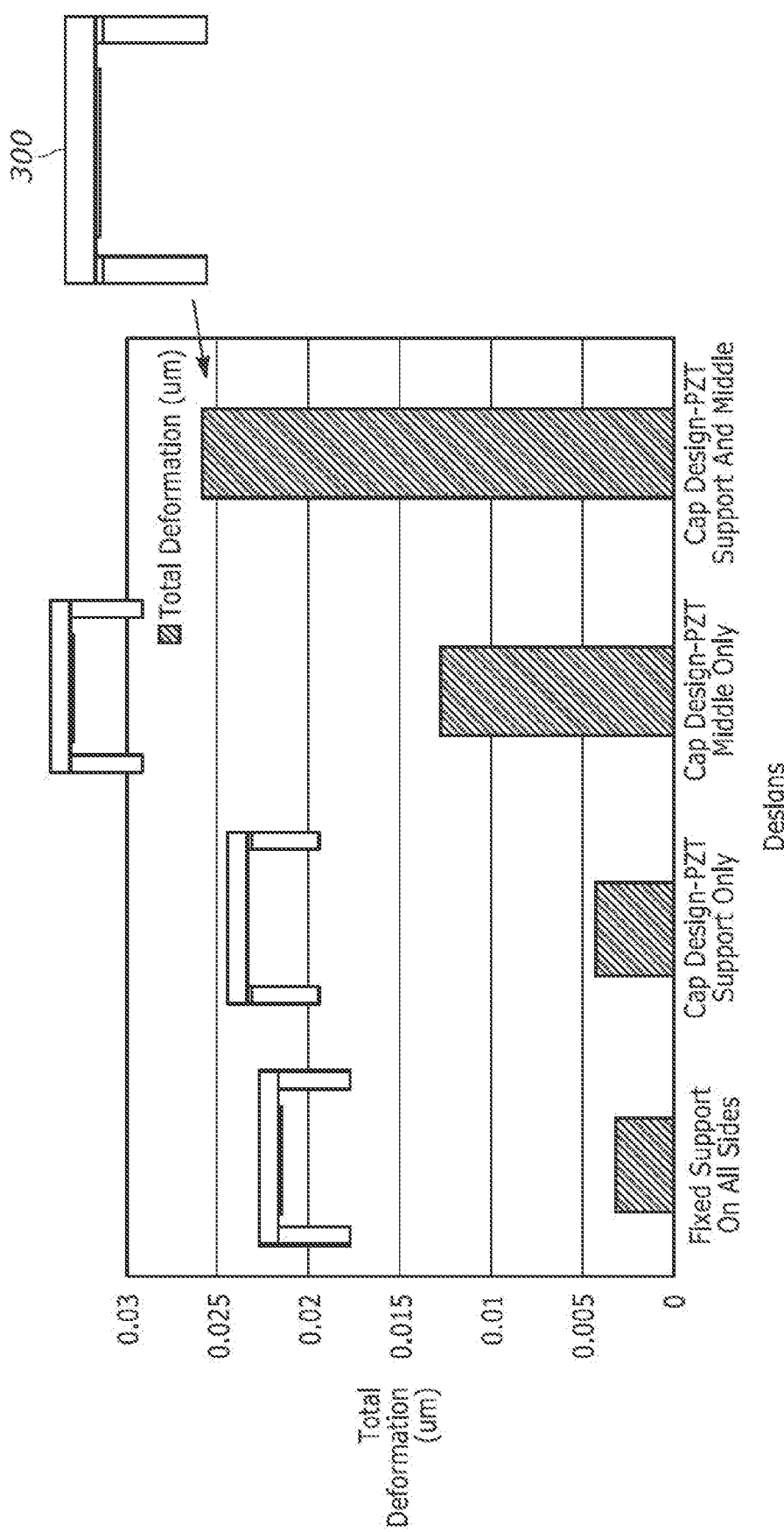
FIG. 4 illustrates a graph comparing various embodiments of the various piston mode designs against total deformation.

FIG. 4 is an illustration of a graph comparing various embodiments of the various piston mode designs against total deformation. The graph may show deformation for the various designs, with the embodiment of the present application at the far right, which includes a piezoelectric layer at the center of the membrane and attaching the support structure and membrane. The graph may show an example of a transducer with a fixed support on all sides, and thus a fixed support may be on each axial side of the membrane and in the center section of the membrane a piezoelectric layer. In another example, the fixed support may be attached to the membrane and the piezoelectric layer. In yet another example, the piezoelectric layer may only be in a center section of the membrane. From simulation, as much as 10X improvement can be achieved with the combination of a bending and piston mode design. This is shown in FIG. 4.

Of course, in an alternative embodiment, if a continuous surface is needed for the system, the whole structure can be connected with a lower Young's modulus material to seal the gap between the transducer and its surrounding system, as long as the material's spring constant is sufficiently low to not restrict the membrane movement on the edges.

With the gasket surrounding the clamped-clamped beam or circular membrane for traditional sensors with thick beam/membrane, it may be highly inefficient to actuate such structure with MEMS deposited in a 2 um thick PZT layer. Therefore, in another embodiment, a piston design with surrounding gasket is shown in FIG. 5. The piston membrane may be actuated by a bending mode cantilever underneath. Translation changes from bending mode to piston mode. With such a design, the energy spend on actuating the thin cantilevers may be more efficient than the energy spend to bend a thick beam.

Figure 5B:
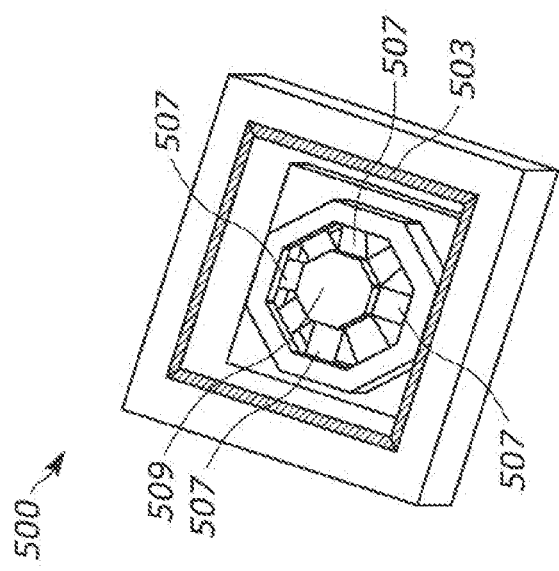
FIG. 5B illustrates a top-view of an embodiment of a transducer, with the membrane removed.
Figure 5A:
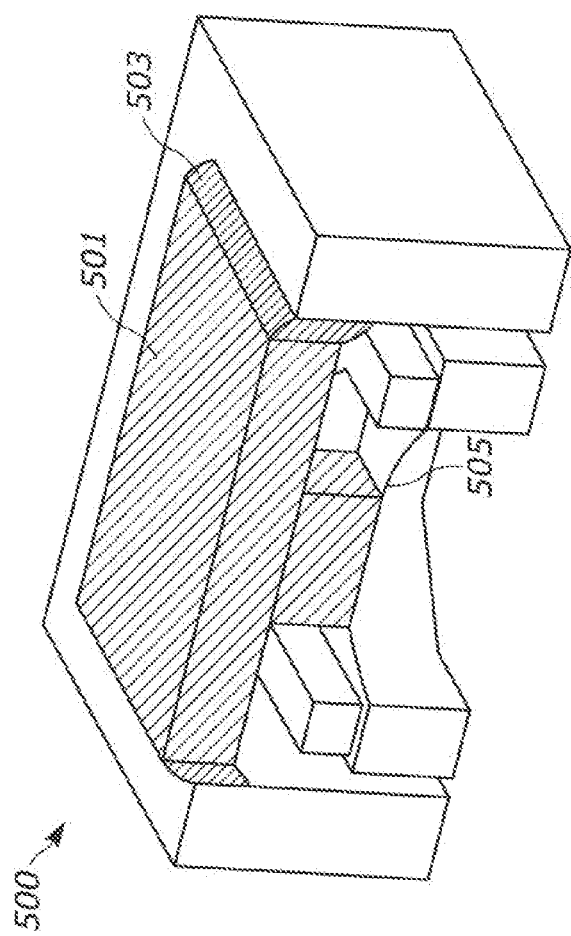
FIG. 5A illustrates a cross-section of an embodiment with a rectangular shaped membrane.

FIG. 5A illustrates a cross-section of a perspective view of an embodiment with a rectangular shaped membrane 501 of a transducer 500. Note that the membrane 501 may act like a piston (e.g., uniformly) while the gasket 503 ring provides sufficient support for sealing against the environment without restricting the movement of the membrane perceptibly. This embodiment can achieve large deflection while still withstanding harsh environments. A cantilever may also be utilized. The cantilever may act as a drive to a piston mode to allow for membrane movement in the area surrounding the gasket 503. The cantilever may include one full surrounding or multiple cantilevers that surround the membrane or a portion of the membrane as utilized to actuate the membrane. The gasket 503 may surround the membrane 501 and be utilized to attach the membrane 501 to the support structure. In such alternative embodiment, the structure may include a series connection of bending mode and piston mode.

Although an embodiment that includes a parallel connection of bending and piston modes can achieve larger displacement for a flexible and thin membrane, deflecting a stiffer and thicker membrane may be more challenging. A parallel connection may refer to placing supports or cantilever beams in a configuration or setting where they may be utilized to add stiffness to the support structure of the transducer. In the alternative embodiment, a bending mode cantilever may be utilized to translate the displacement to a piston-mode membrane. Thus, deflecting a thin and flexible cantilever (~1-100 um) will be easier than deflecting a thick and stiff membrane (>100 um thick). Since thicker membrane (>100 um) may be required for withstanding impact from particles, the thicker membrane may be actuated by the flexible cantilever in a piston mode configuration. In addition, for a continuous surface to the environment, a lower Young's modulus material (e.g., silicone gel or rubber silicone) may be used to seal the ring around the thicker membrane, similar to a gasket where the effect of the gasket is relatively low in restricting the membrane movement on the edges.

In one example configuration of an embodiment for piezoelectric actuation, the cantilever or the bending element should be thinner than 100 um for a piezoelectric thickness of 2 um or correspondingly, thinner than 50 um for a piezoelectric thickness of 1 um. In addition, for an alternative design, the spring constant of the cantilever 505 should be at least one order of magnitude higher than the spring constant of the gasket material such that the variability of the gasket material to temperature or environment has less impact on the overall performance of the transducer. This order of magnitude difference in stiffness ensures the cantilever beam is the dominant stiffness in the system. Therefore, the ultrasonic sensors resonant frequency is mainly determined by the cantilever beams stiffness while changes in the gasket stiffness has little affect. Thus, the resonant frequency is associated with the cantilever beams stiffness. To reduce variation in the resonant frequency, cantilever beams can be made of silicon, which may be more mechanically stable than the typical materials used for gaskets (e.g., rubber or silicone).

A further advantage by using this alternative embodiment with a cantilever is that a piston mode device can be ~½ the size (example above) and still move the same volume of air as opposed to the other embodiments, thus it can be much smaller. Also, for bending membranes it is mandatory to use round or elliptic shape geometries to generate sound and/or ultra sound signals in a wanted directivity in two dimensions. However, the shape of the membrane for a piston movement is not limited in any way. This point is especially important because the membrane shape defines the working volume of a sensor for a sound or ultrasound generator and allows new functionality features as well as possibilities in respect to miniaturization of components.

As shown in FIG. 5B, which illustrates the top view of the device (shown without the membrane), the combination of eight cantilevers 507 are responsible as the driver for the piston movements of the membrane, which has a portion shown in center of cantilevers 509). In such a view of FIG. 5B, the square portion of the membrane is transparent to emphasize the cantilevers 507. The eight cantilevers 507 can be utilized for hosting the piezoelectric materials, which may be utilized to move the square membrane on the top and out-of-plane displacement of the membranes. The gasket 503 may be utilized to attach to outer edges of the membrane, which is not shown in the picture.

Figure 6:
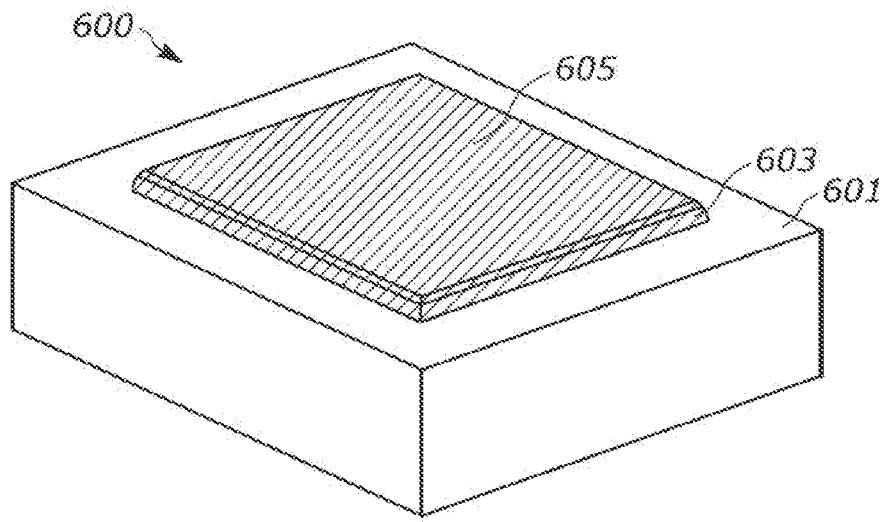
FIG. 6 illustrates a simulated displacement of a piston membrane in a transducer.

FIG. 6 illustrates a simulated displacement of a piston membrane in a transducer 600. As shown in FIG. 6, the membrane 605 and gasket 603 may move in a piston mode.

FIG. 6 shows the simulated displacement of piston membrane 605 at a center section of the piston membrane. Thus, the membrane 605 may be displaced and the rest of the cantilever or other rigid portion 601 (e.g., support structure) of the element may be firm. Thus, when a piston mode of the transducer is actuated, the membrane and gasket allow for movement, while the support structure does not allow for any movement.

Figure 7:
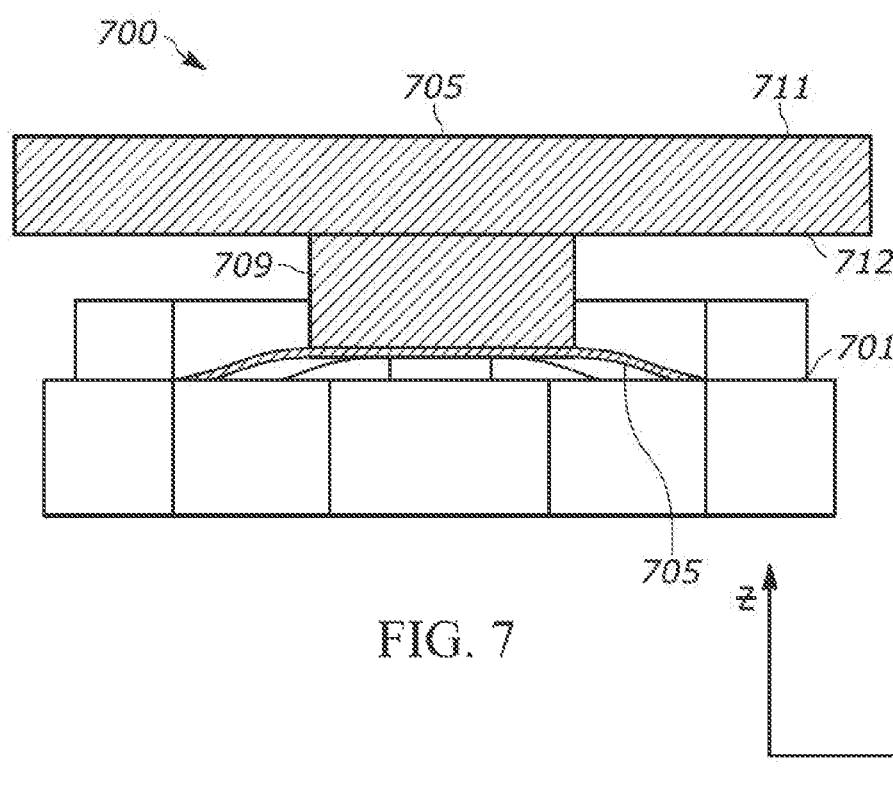
FIG. 7 illustrates a side-view of an actuation of the transducer without a frame or gasket.

FIG. 7 illustrates a side-view of an actuation of the transducer 700. As shown, the membrane 705 is actuated to be out of the plane in the positive z-direction. A top surface of the membrane 711 and bottom surface of the membrane 712 are parallel to one another with no support from the support structure or gasket (not shown in figure). The membrane 705 may include a center portion 709 that connects the bottom surface of the membrane to the cantilever 706 and support structure 701. In such an embodiment, the actuation is out of plane in the positive z-direction as shown, when the membrane 705 is out-of-plane, there may be a gap between the support structure 701 and the membrane 705.

Figure 8:
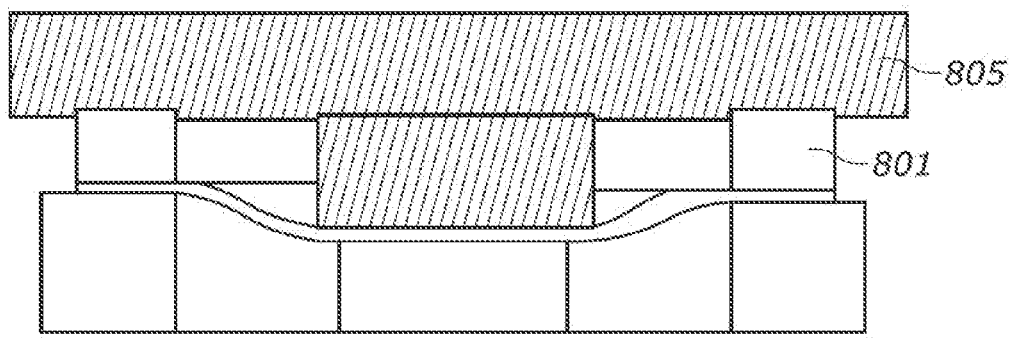
FIG. 8 illustrates an alternative embodiment of a sideview of an actuation of a transducer.

FIG. 8 illustrates another side view/cross-section of an actuation of a transducer 800. As shown, the membrane 805 may have actuation out of plane in the negative z-direction (or radially inward in the side-view perspective). The membrane 805 may be connected to the support structure 801 as it was described in FIG. 7. Thus, when the membrane 805 is actuating out-of-plane in the negative z-direction, the membrane 805 may be in contact with or close to the support structure 801. Thus, FIG. 7 and FIG. 8 show the actuation of the transducer (gasket is not shown for better illustration), where the FIG. 7 shows the actuation out-of-plane in the positive z-direction and FIG. 8 shows the actuation out-of-plane in the negative z-direction.

Figure 9:
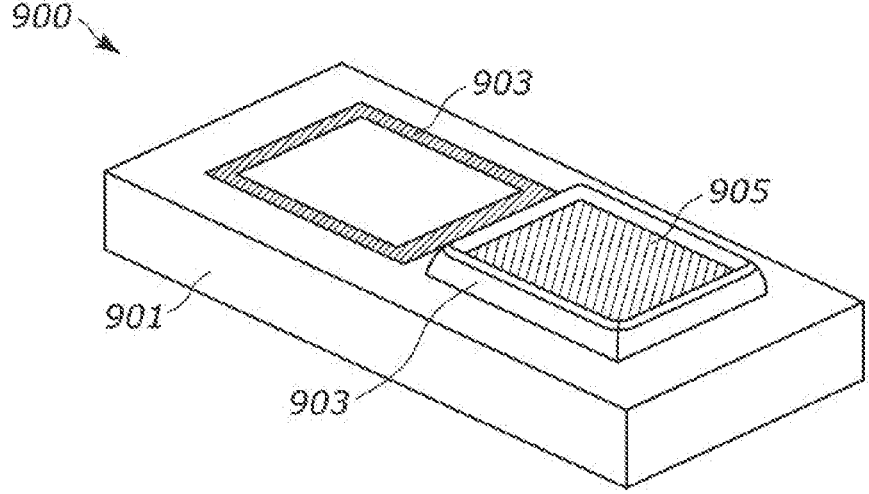
FIG. 9 illustrates an embodiment of an array with two transducers in a support structure.

FIG. 9 illustrates an embodiment of an array 900 of two transducers membranes 905 in a support structure 901 showing one actuated in a piston mode with the positive z-direction (e.g. 905a) and the other in the negative z-direction (e.g. 905b). In such an embodiment, there is a two element array configuration. In such an embodiment, the actuation of one piston membrane 903 does not affect the other membrane during actuation (e.g., no cross coupling effect here). These individual element can be duplicated into multiple elements arranged in array configurations. For example, there may be any number of transducers in an array. The transducers 905(a,b) may act synchronously or asynchronously (e.g., as shown in FIG. 9.). More examples of the arrays and frames are discussed below.

Figure 10A:
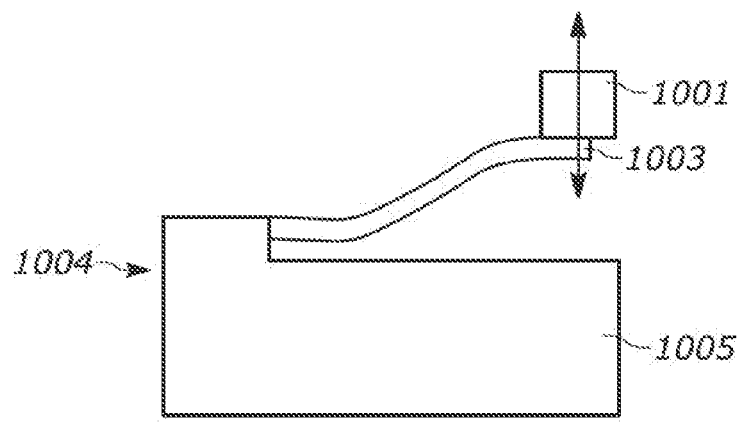
FIG. 10A shows an example of a side-view of a transducer utilizing a hard-stop implementation at the bottom.

FIG. 10A shows an example of a side-view of a cantilever actuator utilizing a hard-stop implementation at the bottom. As shown, the cantilever 1003 may have one end attached to the support structure 1004 and one end at the membrane 1001 or a connection portion attached to the membrane. The hard stop 1005 may be on the bottom preventing the cantilever 1003 from moving inwards pass a fracture point. Thus, it may prevent breakage and failure of the cantilever 1003 during actuation. Additionally, the hard stop 1005 may be formed as a part of the support structure 1004. Thus, the hard stop portion 1005 may extend axially out from the support structure 1004. Thus, both the hard stop 1005 and the support structure 1004 may extend axially out.

Figure 10B:
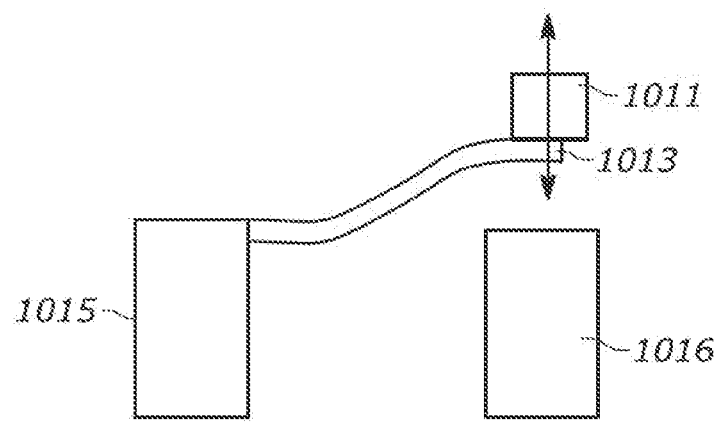
FIG. 10B shows an example of a hard-stop implementation extending radially outwards.

FIG. 10B shows an example of a hard-stop implementation extending radially outwards with a gap between the support structure 1015. The cantilever 1013 may be attached to the membrane 1011 at one end. The hard stop 1016 in such an implementation may prevent the cantilever 1013 from moving downwards pass a fracture point. As shown in such an embodiment, the cantilever 1013 may extend axially away from the support structure 1015. However, the hard stop 1016 implementation may prevent the cantilever 1013 from radial movement inwards towards the axis and in-plane movement. In such an embodiment, the stoppage may occur at a top surface of the hard stop 1016.

Figure 10C:
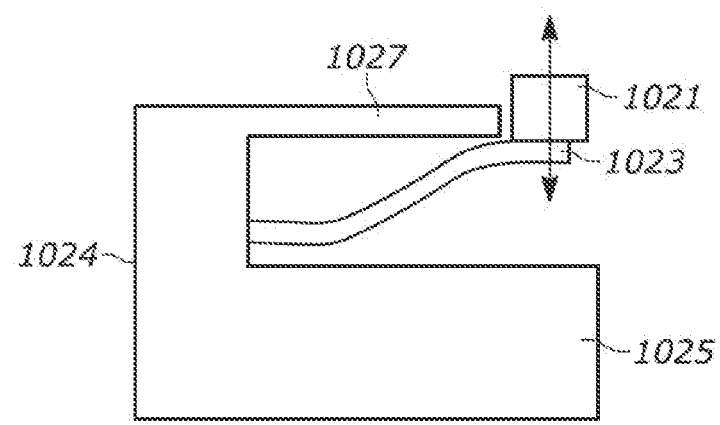
FIG. 10C shows an example of a side-view of a transducer utilizing a hard-stop implementation at the top of the support structure.

FIG. 10C shows an example of a side-view of a cantilever actuator utilizing a hard-stop implementation at the top of the support structure 1024. In such an embodiment, the hard stop 1025 may extend radially outward away from a point of the support structure 1024 that is radially outward in comparison to the cantilever 1023. Thus, the hard stop portion may extend axially out from the support structure 1024. In addition to the design of bending to piston movement, a hard stop can also be implemented on one or both sides of the cantilever to restrict further displacement (push or pull force) than bending past the cantilever's fracture point. Thus, a bottom hard stop 1025 may be implemented to prevent the movement from becoming radially inward. And the top hard stop 1027 may prevent radially upward movement. With the hard stop, the piston membrane 1021 can further withstand harsh environment.

Figure 11:
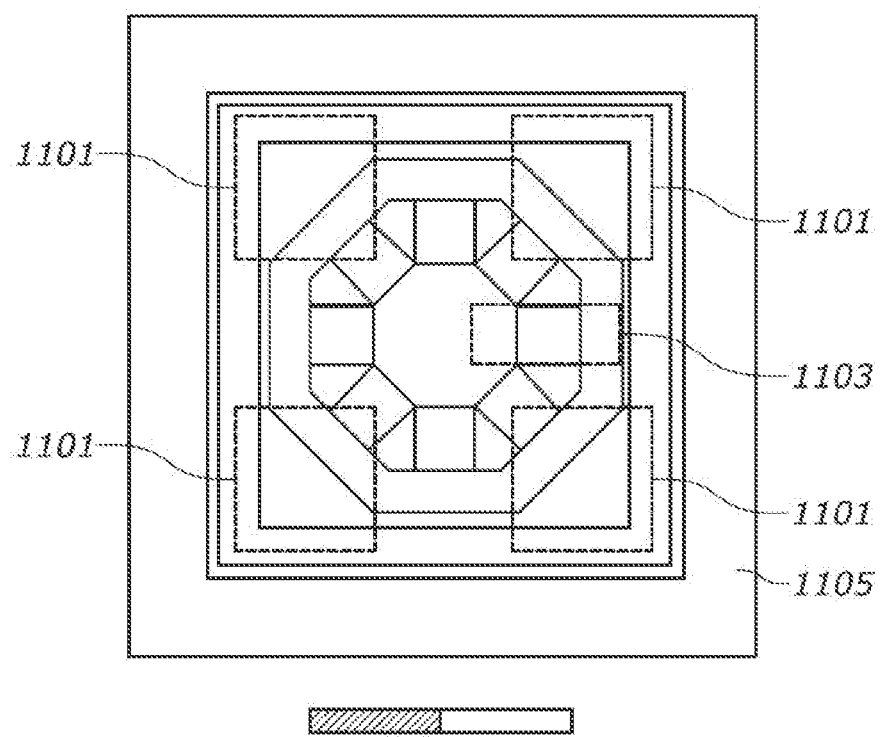
FIG. 11 discloses an embodiment of a top-view perspective of a bending cantilever.

FIG. 11 is an example of a top view of a bending cantilever. The structure includes the bending cantilevers has unused corners 1101 which are there purely for connecting the supports. The area may not be needed and can increase the overall cost of fabricating such device. Additionally, the added weight of the mass can add to the overall weight of the vehicle. The functional area 1103 may be utilized to provide actual support to the bending cantilever. Thus, the functional area 1103 may be required to have a sufficient secure and rigid structure. The frame 1105 may provide support for the structure.

Figure 12:
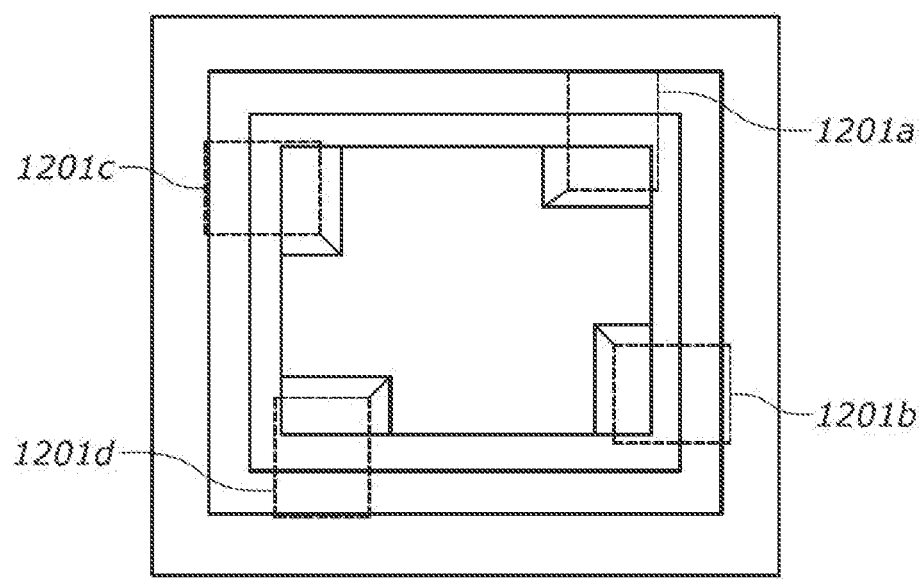
FIG. 12 discloses an embodiment of a top-view perspective view with distributed cantilevers.

FIG. 12 discloses an embodiment of a top-view perspective view with distributed cantilevers. On the other hand, in FIG. 12, with distributed cantilevers, the area is optimally utilized for cantilevers without waste of area. With a lower area needed for the cantilevers, the cost can be reduced as it may reduce materials utilized and fabrication costs. The transducer 1200 may include a functional area needed for each cantilever. In the instance, there may be four functional areas 1201a, 1201b, 1201c, 1201d for each associated cantilever. Thus, the cantilever in such an embodiment may get rid of material not needed (e.g., silicon material) and spread out the cantilevers. The membrane may be one solid material. The membrane may be bigger than the cantilever.

Figure 13A:
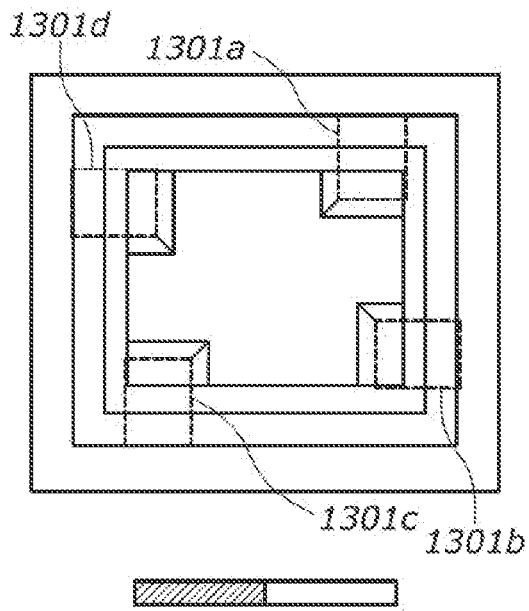
FIG. 13A discloses a first embodiment of a displacement configuration of the cantilevers with respect to the piston membrane.
Figure 13B:
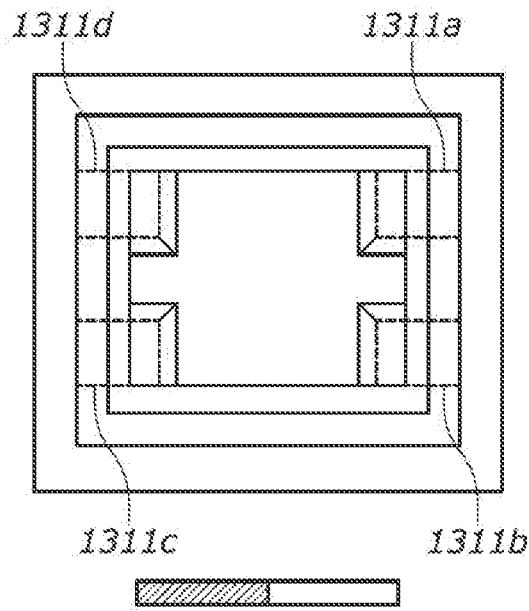
FIG. 13B discloses a second embodiment of a displacement configuration of the cantilevers with respect to the piston membrane.
Figure 13C:
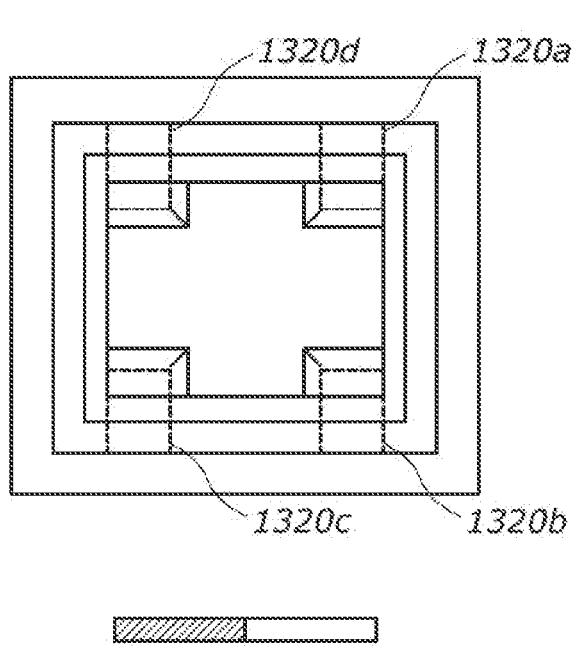
FIG. 13C discloses a third embodiment of a displacement configuration of the cantilevers with respect to the piston membrane.
Figure 13D:
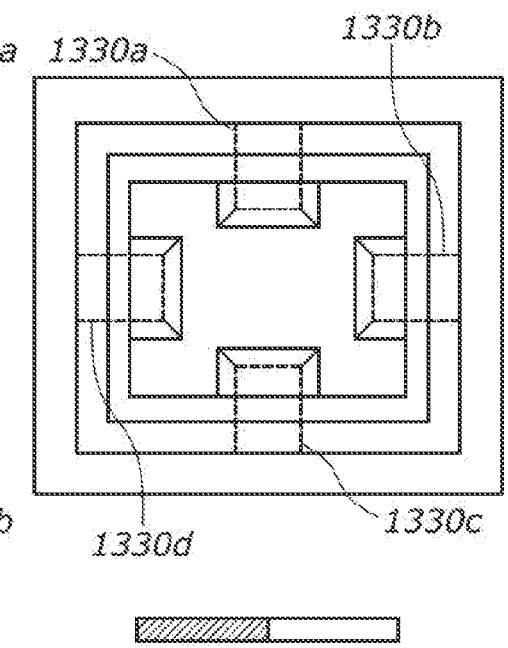
FIG. 13D discloses a fourth embodiment of a displacement configuration of the cantilevers with respect to the piston membrane.

FIG. 13A discloses a first embodiment of a displacement configuration of the cantilevers with respect to the piston membrane. In such a design, the functional area 1301a, 1301b. 1301c, 1301d may be located on four corners of an inner perimeter of the frame/substrate of the transducer. The functional area may have rectangular or square supports extending away from the perimeters on each of the four sides for utilization as a functional area of the cantilevers. FIG. 13B discloses a second embodiment of a displacement configuration of the cantilevers with respect to the piston membrane. In such an embodiment, the functional area 1311a, 1311b, 1311c, 13011d is extending away from only two parallel sides of the inner perimeter of the membrane. Thus, two of the sides do not have any functional areas being utilized, however, they may be adjacent. FIG. 13C discloses a third embodiment of a displacement configuration of the cantilevers 1320a, 1320b, 1320c, 1320d with respect to the piston membrane. FIG. 13D discloses a fourth embodiment of a displacement configuration of the cantilevers 1330a, 1330b, 1330c, 1330d with respect to the piston membrane. Thus, FIGS. 13A-13D show examples of different placement and configurations of the cantilevers with respect to the piston membrane. The first mode resonance frequency, as well as higher mode resonance frequencies, may be determined by the placement of the cantilevers, as well as the orientation of the cantilevers with respect to the membrane. For certain configurations, the rocking mode frequency might be lower than the piston mode frequency which is not desired.

Figure 14A:
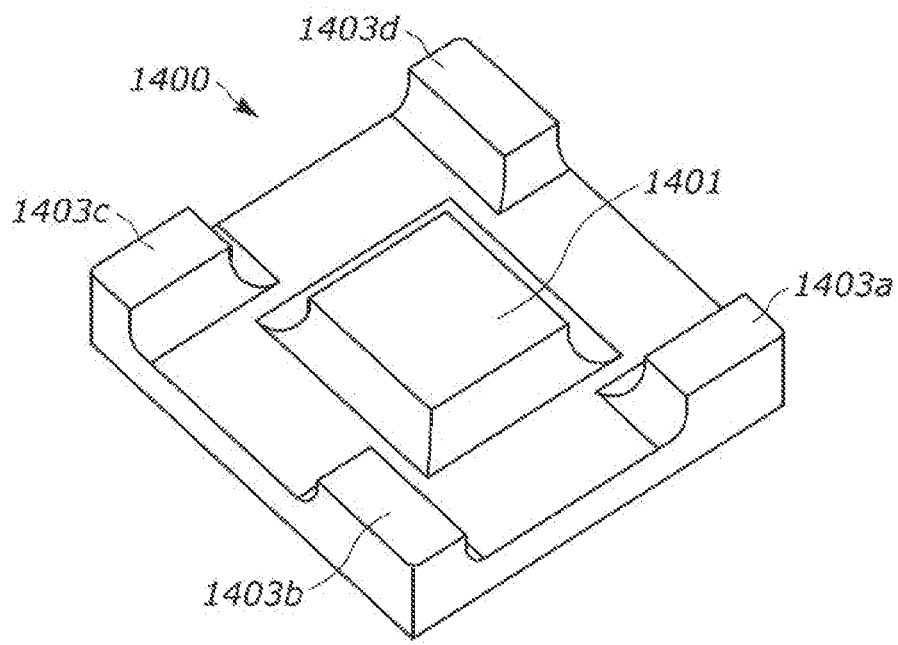
FIG. 14A discloses an embodiment of a bottom-view perspective of an alternative embodiment with added mass to the center of the piston membrane.

FIG. 14A discloses an embodiment of a bottom-view perspective of an alternative embodiment of the membrane 1400. The membrane 1400 may include an added mass 1401 to the center of the piston membrane 1400. The added mass 1401 may be located at the center of the membrane. By decoupling the design of the cantilevers from the platform or membrane 1400 of the ultrasound transducers, it is easier and more convenient to scale or change the transducer design. The membrane 1400 may include membrane feet 1403*a*, 1403*b*, 1403*c*, 1403*d*. The membrane feet may all have different configurations to coincide and match the distributed cantilever embodiments, as shown above. The membrane feet 1403*a* may extend in the bottom right corner and abut the bottom side of the perimeter. The membrane feet 1403*b* may extend in the bottom left corner and abut the left side of the perimeter. The membrane feet 1403*c* may extend from a top-left corner and abut the top side. The membrane feet 1403*d* may extend from a top-right corner and abut the right side.

Figure 14B:
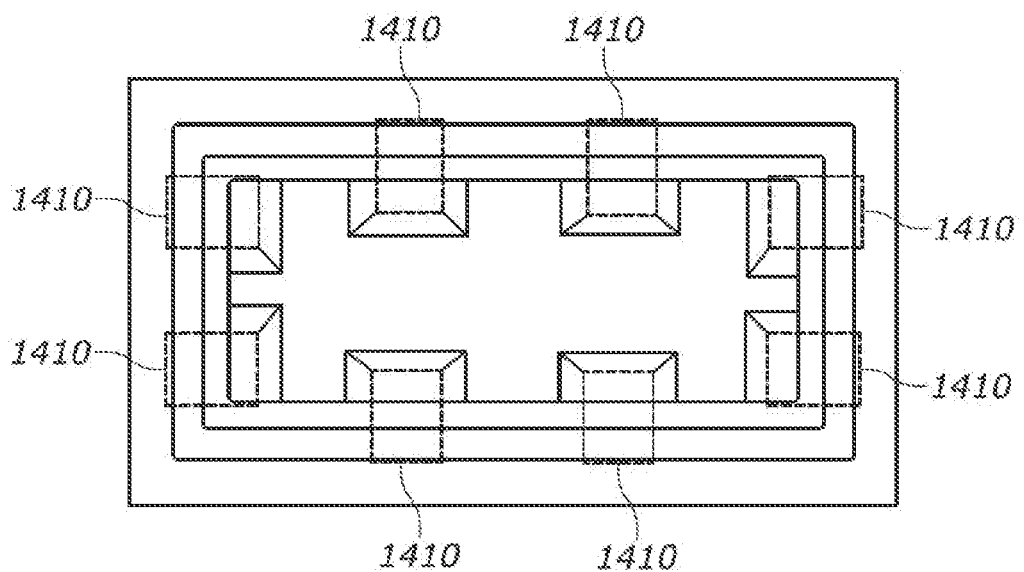
FIG. 14B discloses an embodiment of a displacement configuration of the cantilevers with respect to the piston membrane with eight cantilevers.

FIG. 14B discloses an example of the cantilever design attaching to a platform of the membrane. In such an example, in the case where the platform or membrane needs to be enlarged (e.g. sound pressure level or opening angle of sound waves), the cantilever design can remain the same while just changing the thickness of the cantilever or using a different number of cantilevers in order to maintain the same resonance frequency. This makes the design versatile. In such an embodiment, the functional area 1410 may be needed for each cantilever.

Figure 15A:
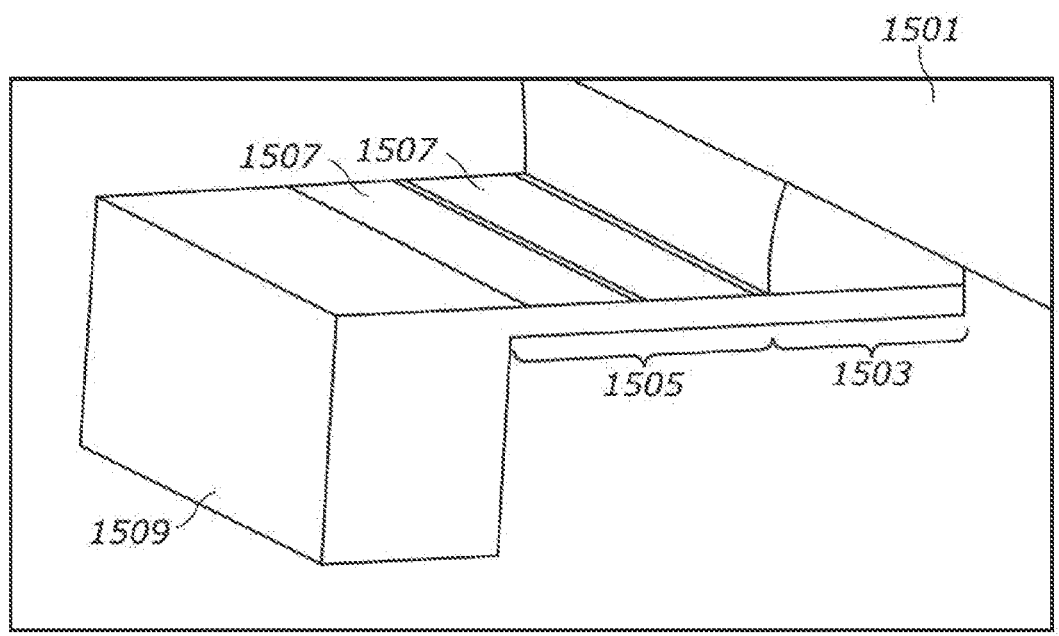
FIG. 15A discloses an illustrative embodiment of a cantilever with a suspended portion attached to the membrane.

FIG. 15A discloses an example of cantilever with a suspended portion attached to the membrane. The membrane 1501 may also be a platform. The membrane 1501 may include a foot that extends away from a bottom surface of the membrane 1501 and attaches to the cantilever. The cantilever may include a connection portion 1503 that connects to the membrane 1501. The cantilever may also include a suspended cantilever portion 1505 that is suspended above a PCB or another substrate or structure. The cantilever may include a piezoelectric layer 1507. The piezoelectric layer 1507 may include a two or more with opposite polarities, as well as a single layer in an alternative embodiment. The cantilever may also include a support portion 1509 that attaches to the substrate (e.g., PCB). Thus, the cantilever may include the suspended portion 1505, the connection portion 1503, and the support portion 1509. Although in this disclosure, piezoelectric or lead zirconate titanate (PZT) actuation and sensing is described as an example, the method can be expanded to electrostatic actuation or capacitive sensing as well as electromagnetic and etc. In addition, the transducer can function as a sensing device, a transmitting device or both as a sensing and transmitting device.

Figure 15B:
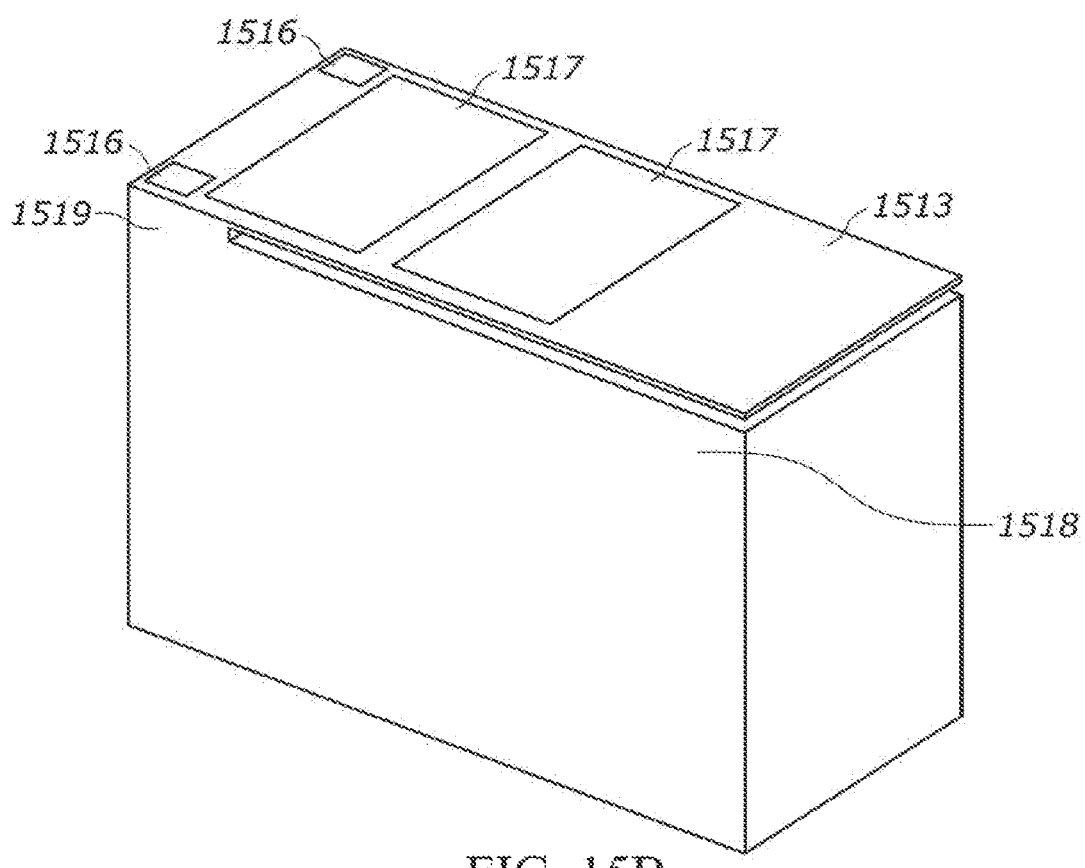
FIG. 15B discloses an illustrative embodiment of a cantilever with a substrate acting as a hard stop.

FIG. 15B discloses an illustrative embodiment of a cantilever with a substrate acting as a hard stop. The first piezoelectric layer portion 1517 and second piezoelectric layer 1517 portion may be on the suspended cantilever portion. The first piezoelectric layer portion and second piezoelectric layer portion may have opposite polarities, for example. While the cantilever may extend away from the support portion 1519, which is a part of the substrate 1518, at one end of the cantilever, and attach to a stub (not shown) or membrane on an opposite end of the cantilever 1513. The cantilever 1513 may include a bond electrical connection 1516 to connect to wires or other components of the transducer or vehicle system.

Figure 15C:
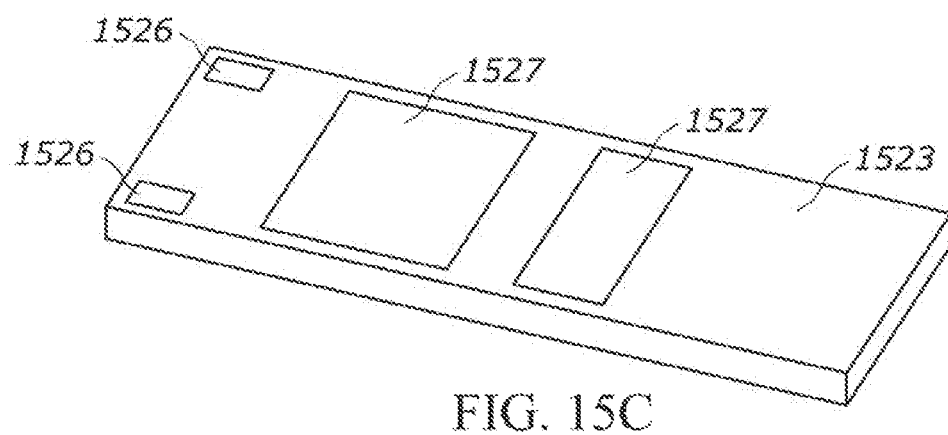
FIG. 15C discloses an example embodiment of a cantilever portion independent of being attached to a substrate.

FIG. 15C discloses an embodiment of a cantilever 1523 by itself and not attached to a substrate. The cantilever may include one or more piezoelectric layers 1527. The piezoelectric layers 1527 may be opposite polarities in one embodiment, or steered phased shifted in another embodiment. The piezoelectric layers 1527 may either be all the same size or different sizes. In such an embodiment, the cantilever 1523 may be a separate material from the components of the transducer, such as the support, hard stop, or substrate. The cantilever 1523 may be connected via an adhesive or mechanical connection to another component. The cantilever 1523 can then be mounted onto another substrate (e.g., PCB). The cantilever 1523 may include a bond electrical connection 1526 to connect to wires or other components of the transducer or vehicle system.

Figure 16A:
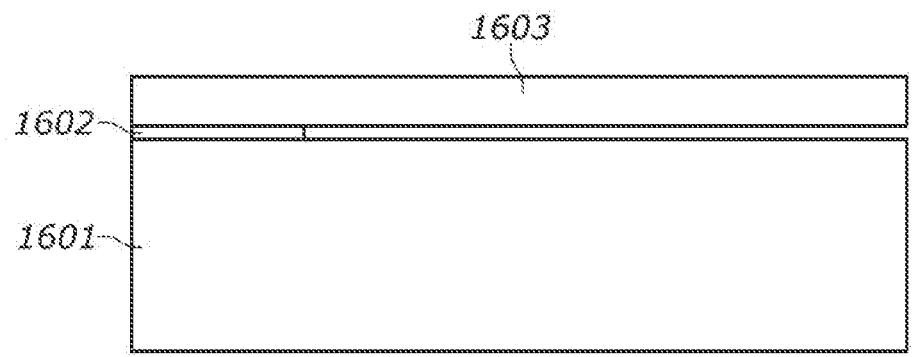
FIG. 16A discloses an embodiment that utilizes a small additional layer between the cantilever and the substrate.

FIG. 16A discloses an embodiment that utilizes a small layer (e.g. seal glass, epitaxic grown silicon, glue, etc.) between the cantilever and the substrate. The cantilever 1603 may be connected to the substrate 1601 via an adhesive layer 1602. The adhesive layer 1602 may be a glue layer, glass, or any other type of material to attach the cantilever 1603 to the substrate 1601. The height of the component may be adjusted based upon the height of the adhesive layer 1602. Thus, the more the adhesive layer 1602, the air gap between the bottom surface of the cantilever 1603 and the top layer of the substrate 1601 increases.

Figure 16B:
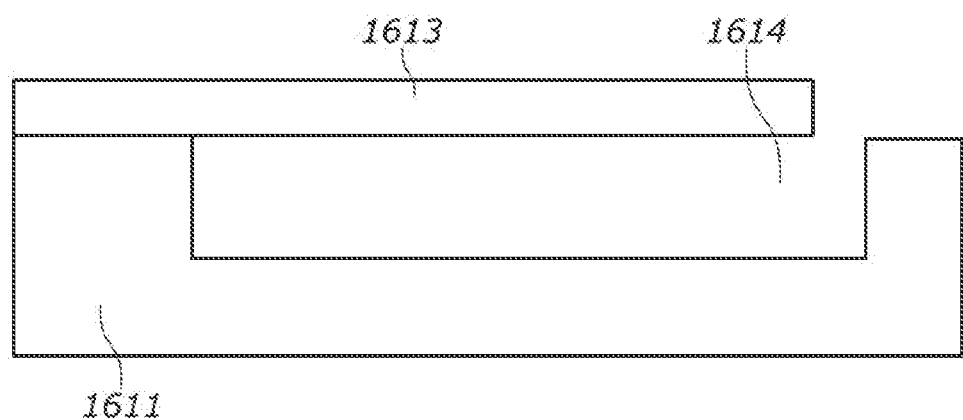
FIG. 16B discloses an embodiment that includes a cavity between the cantilever and substrate.

FIG. 16B discloses an embodiment that includes a cavity between the cantilever and substrate. The cavity 1614 may be defined by a bottom surface and side surfaces of the substrate 1611. The cavity 1614 may allow for the cantilever 1613 more flexibility in bending, as it eliminates much of the hard stop that a substrate 1611 typically offers. The cavity 1614 may be any shape and size to allow for additional bending of the cantilever.

Figure 17A:
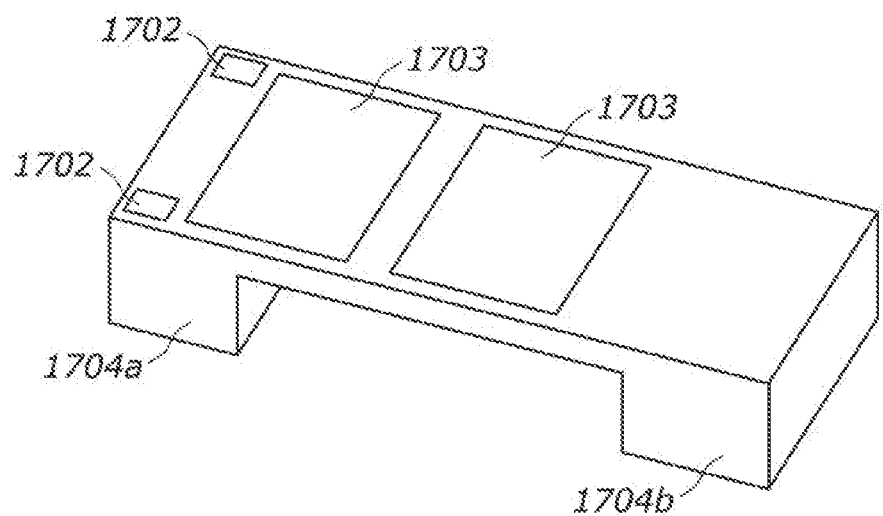
FIG. 17A illustrates an embodiment of a cantilever with bottom stubs at the cantilever.
Figure 17B:
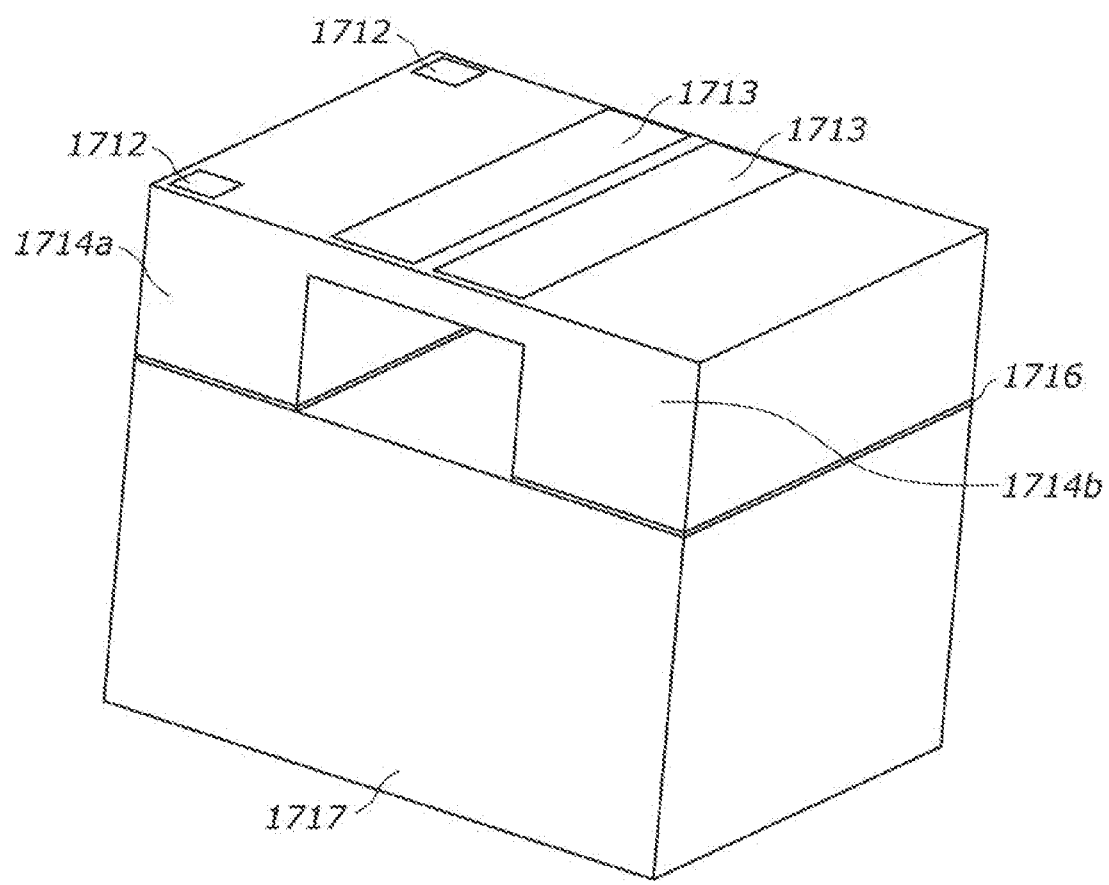
FIG. 17B discloses an embodiment of a cantilever with stubs at both ends and connected to a substrate.

FIG. 17A illustrates an embodiment of a cantilever with bottom stubs at the cantilever. The electrical bonds 1702 may be utilized to connect to various wires to the cantilever. The cantilever may include a first stub 1704*a* and a second stub 1704*b*. In such an embodiment, the cantilever is shown with the stubs 1704*a*, 1704*b* but not attached to any substrate and is thus in isolation. In one embodiment, the stubs 1704*a*, 1704*b* may not have the same height but could be a different height. In another embodiment, the stubs FIG. 17B discloses an embodiment of a cantilever with stubs at both ends and connected to a substrate. In order to prevent damage of a cantilever due to bending past the fracture point, a hard stop may be seen to avoid such damage. Break off of a cantilever could occur for a bending in the magnitude of only a 1-50 um (or smaller or larger). In such an embodiment, as opposed to the embodiment of FIG. 15B, the cantilever is not one continuous component but a component with stubs 1741*a*, 1741*b* attached to both ends. A gap 1716 may exist between one end of the stub 1741*b* that may allow for some flexibility. The hard stop 1717 may be implemented to mitigate extreme bending and to prevent breakage of flexibility. A piezoelectric layer 1703 may include opposite polarities in one embodiment. The hard stop 1717 may be a separate component or one continuous component of the cantilever in alternative embodiments. The electrical bond pad 1712 may be utilized to connect to various wires to the cantilever.

Figure 17C:
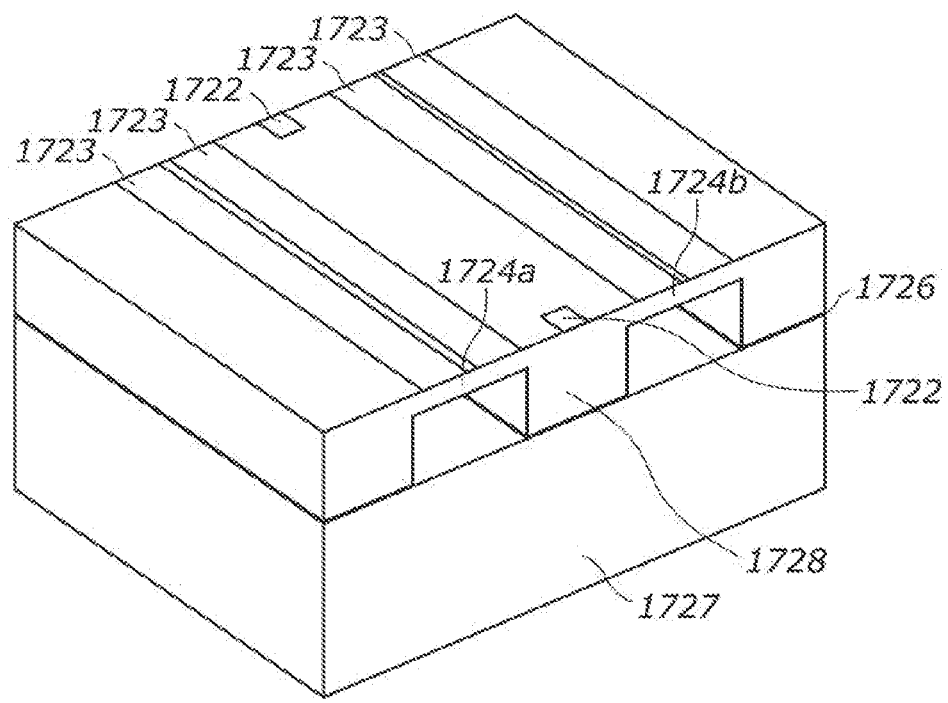
FIG. 17C discloses an embodiment utilizing two cantilevers.

FIG. 17C discloses a design utilizing two cantilevers. The two cantilevers 1724a, 1724b can be connected by a common middle stub 1728 (e.g., middle pillar), which is connected with a hard stop protection. The hard stop protection maybe made of silicon. An electrical bonding connection may be located 1722 to allow for actuation via electrical wires. A gap 1726 may allow for free oscillating of the cantilevers. The gap 1726 may be typically between 1-50 um. The gap 1726 may be formed between a bottom portion of the support portion of the cantilevers 1724a, 1724b or the middle pillar 1728. Multiple piezoelectric layers 1723 may be included and placed on the cantilever. The piezoelectric layers 1723 may be in pairs where each pair includes opposite polarities within that group.

Figure 18:
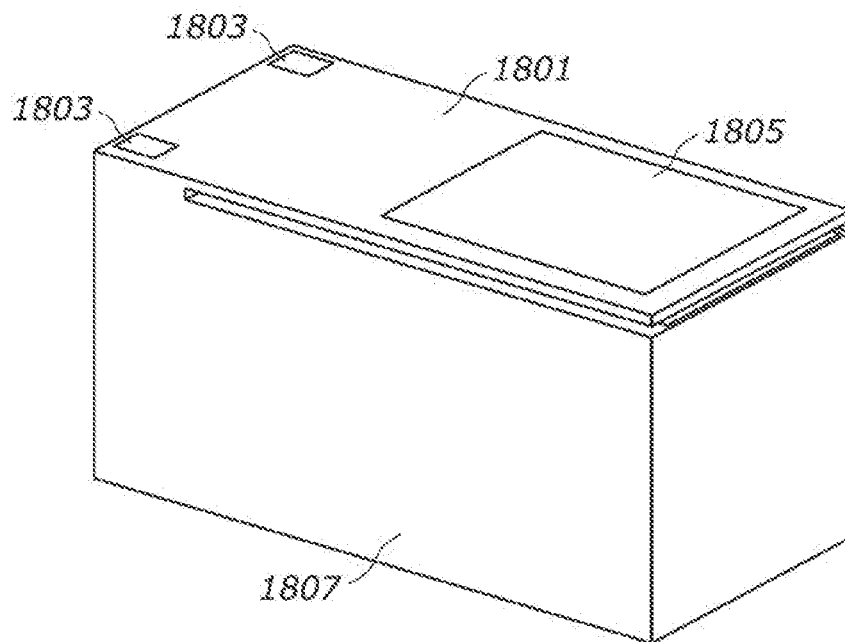
FIG. 18 discloses an embodiment of a cantilever that utilizes electrostatic actuation.

FIG. 18 discloses a cantilever that utilizes electrostatic actuation. Electrostatic actuation may be utilized as an alternative to a piezoelectric layer. In such an embodiment, electrodes may be deposited on both the cantilever 1801 and the substrate 1807. Although the electrode 1805 on the cantilever is shown on top in the picture, the electrode can also be configured to be on the bottom of the cantilever. In various embodiments, the electrode 1805 may be either on the top or bottom of the cantilever, as well as both on the top and the bottom of the cantilever 1801. The cantilever 1801 may include an electrical bonding connection 1803 to connect wires to the cantilever 1801 for actuation. In an embodiment when the electrode is on the bottom of the cantilever, the mounting of the platform may be impeded by the location of the electrode.

Figure 19A:
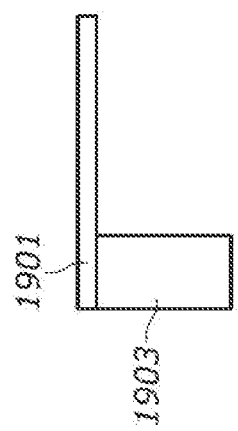
FIGS. 19A-19F discloses various embodiments of cantilevers with a free-end.
Figure 19B:
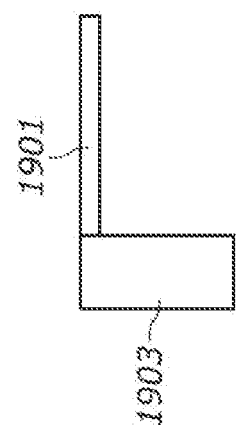

FIGS. 19A-19F discloses various cantilevers with a free-end and with distributed mass on top of the cantilever. FIG. 19A discloses a cantilever 1901 that is attached to a top surface of a support structure 1903. The cantilever 1901 may include various shapes and sizes, such as a round shape, rectangular shape, etc. A platform may be utilized as a cantilever. The platform may include an air gap between the substrate and a bottom of the platform. In various embodiments, the platform may also include a bridge design or a diaphragm design, in addition to the cantilever design. The platform may be any shape, such as rectangular, circular, round, etc. In such an embodiment, the cantilever may have an anchor bottom at the support structure 1903 that prevents movement of the cantilever or flexing of the cantilever. FIG. 19B discloses a cantilever 1901 attached to a side of support structure 1903, as opposed to a top surface.

Figure 19C:
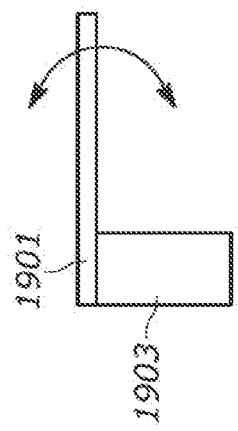
Figure 19D:
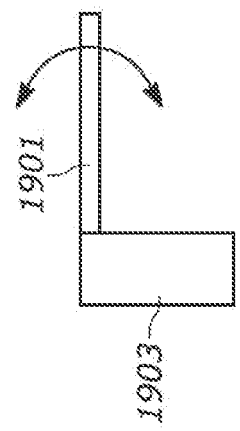

FIG. 19C discloses a cantilever 1901 attached to a top surface of a support structure 1903. In such an embodiment, the cantilever may have flexibility to move up and down at an opposite end of the support structure. Unlike the embodiments above, there may be no anchor bottom that prevents movement of the cantilever or flexing of the cantilever. FIG. 19D discloses a cantilever 1901 attached to a side of a support structure 1903. In such an embodiment, there is no anchor on the side of the support structure, thus the cantilever 1901 may have displacement of a free-end.

Figure 19E:
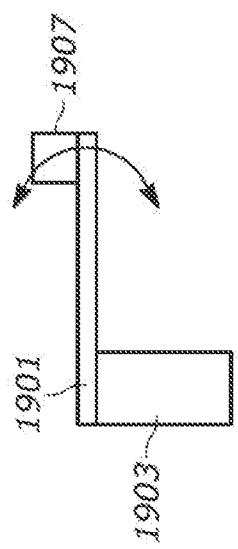
Figure 19F:
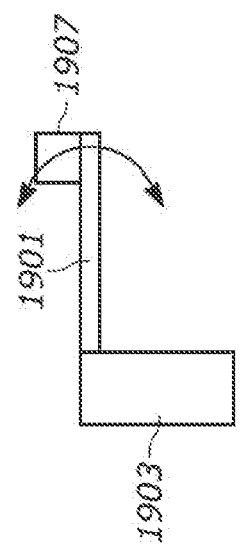

FIG. 19E discloses a cantilever 1901 attached to a top surface of a support structure 1903 with a support mass 1907. In such an embodiment, the cantilever may have flexibility to move up and down at an opposite end of the support structure. Unlike the embodiments above, there may be no anchor bottom that prevents movement of the cantilever or flexing of the cantilever. FIG. 19F discloses a cantilever 1901 attached to a side of a support structure 1903 with a support mass 1907. In such an embodiment, there is no anchor on the side of the support structure, thus the cantilever 1901 may have displacement of a free-end. The cantilever 1901 may also include a support mass 1907 that may be the membrane of an ultrasound sensor, or an attachment to the membrane. Thus, there are various embodiments that may be utilized in the ultrasound transducer in terms of a cantilevers attachment to the distributed mass and a support structure.

FIG. 20A discloses a cantilever 2001 attached to a top surface of a support structure 2003. FIG. 20A discloses a cantilever 2001 that is attached to a top surface of a support structure 2003. In such an embodiment, the cantilever may have an anchor bottom at the support structure 2003 that prevents movement of the cantilever or flexing of the cantilever. FIG. 20B discloses a cantilever 2001 attached to a side of support structure 2003, as opposed to a top surface. As shown in such an embodiment, the cantilever moves up towards the distributed mass as it moves away from the end attached to the support structure.

FIG. 20C discloses a cantilever 2001 attached to a top surface of a support structure 2003. In such an embodiment, the cantilever may have flexibility to move up and down at an opposite end of the support structure. Thus, the free-end is fixed and guided. In such an embodiment, the cantilever 2001 may be guided and thus not flat and parallel with a substrate. The difference between the free-end cantilever and the fixed-guided beam may be in the trajectory of the moving end. One side may be fixed to the substrate and doesn't move at all. The other side may be allowed to swing freely along a curved trajectory in the free-end cantilever. In other words, the beam bends around the fixed end without anything on the moving end restraining the movement. Therefore, there may be no inflection point. In the fixed-guided beam, the moving end may be constrained to be parallel to the substrate. Thus, the beam may be parallel to the substrate at both ends. One end is allowed to move up and down, while the other is anchored or attached to the substrate. This may force an inflection point in the center and results in the "S" shape of the displaced beam. Unlike the embodiments above, there is no anchor bottom that prevents movement of the cantilever or flexing of the cantilever. FIG. 20D discloses a cantilever 2001 attached to a side of a support structure 2003. In such an embodiment, there is no anchor on the side of the support structure, thus the cantilever 2001 may have displacement of a free-end. In such an embodiment, the free-end 2005 is fixed and guided.

FIG. 20E discloses a cantilever 2001 attached to a top surface of a support structure 2003. In such an embodiment, the cantilever may have flexibility to move up and down at an opposite end of the support structure. Thus, the free-end is fixed and guided. In one embodiment, there may be no anchor bottom that prevents movement of the cantilever or flexing of the cantilever. FIG. 20F discloses a cantilever 2001 attached to a top surface of a support structure 2003. In such an embodiment, there is no anchor on the side of the support structure, thus the cantilever 2001 may have displacement of a free-end. In such an embodiment, the free-end 2005 is fixed and guided.

A bridge, on the other hand, is similar to a cantilever, where the most common configuration is where both of the shorter edges of the rectangular bridge are fixed to supports while the longer edges are free to bend or deflect. The embodiment may be fully clamped membrane and diaphragm to where all edges are bounded or fixed to a support. Only the center of the membrane and diaphragm bends or deflects.

FIG. 21A discloses a bridge 2101 connected to a left support structure 2103a and a right support structure 2103b. The anchors may be at the bottom of the bridge 2101 to connect to left and right support structure. The bridge may be similar to the cantilever in that it both of the shorter edges of the rectangular bridge are fixed to support while the longer edges are free to bend or deflect. In such an embodiment, the anchors may be on a bottom surface of the bridge.

FIG. 21B discloses a bridge 2101 connected to a left support structure 2103a and a right support structure 2103b on a left end 2120 and a right end 2120 of the bridge 2101. Thus, instead of a bottom surface of the bridge 2101 resting on the support structures, the ends of the bridge are connected to the support structure. In such an embodiment, the anchors may be on the side of the bridge.

FIG. 21C discloses a bridge 2101 connected to a left support structure 2103a and a right support structure 2103b which includes a bend 2115 at the center of the bridge 2101. The anchors may be at the bottom of the bridge 2101 to connect to left and right support structure. The bridge may be similar to the cantilever in that it both of the shorter edges of the rectangular bridge are fixed to support while the longer edges are free to bend or deflect. In such an embodiment, the anchors may be on a bottom surface of the bridge. The bridge may allow for some flexibility and bending.

FIG. 21D discloses a bridge 2101 connected to a left support structure 2103a and a right support structure 2103b which includes a bend 2115 at the center of the bridge 2101. The anchors may be at the side of the bridge 2101 to connect to left and right support structure at the side, as opposed to a surface. The bridge may be similar to the cantilever in that it both of the shorter edges of the rectangular bridge are fixed to support while the longer edges are free to bend or deflect. The bridge may allow for some flexibility and bending.

FIG. 21E discloses a bridge 2101 connected to a left support structure 2103a and a right support structure 2103b which includes a bend 2115 at the center of the bridge 2101 that includes a distributed mass 2117 at the bend 2115. The anchors may be at the bottom of the bridge 2101 to connect to left and right support structure. The bridge may be similar to the cantilever in that it both of the shorter edges of the rectangular bridge are fixed to support while the longer edges are free to bend or deflect. In such an embodiment, the anchors may be on a bottom surface of the bridge. The bridge may allow for some flexibility and bending.

FIG. 21F discloses a bridge 2101 connected to a left support structure 2103a and a right support structure 2103b which includes a bend 2115 at the center of the bridge 2101 including a distributed mass 2217 at the bend 2215. The anchors may be at the side of the bridge 2101 to connect to left and right support structure at the side, as opposed to a surface. The bridge may be similar to the cantilever in that both of the shorter edges of the rectangular bridge are fixed to support while the longer edges are free to bend or deflect. The bridge may allow for some flexibility and bending.

As shown in the figures and description above, such as FIG. 6, the piston diaphragm may be deflected upwards in a uniform way, while a support portion or frame or cap of the piston structure may have no deflection. Such a piston diaphragm can also be driven with cantilevers or bridges or a membrane from the bottom. For example, FIGS. 5A and 5B show such examples utilizing cantilevers. All in all, the resonance frequency of such systems can be modelled form equations similar to a mass spring system of cantilever. While cantilevers are shown, bridges and diaphragms may be utilized as well.

The frequency response characteristics of the mass-spring system may be determined by the cantilever's dimensions, which may determine the spring constant as well as the mass of the system. In a simple mass-spring system with distributed mass load, it may be assumed that the distributed mass load is completely stiff. However, in the system where the mass is flexible, the frequency response determination is more complicated and depends additionally on the stiffness of the distributed mass load. Finite element modeling (FEM) may be utilized as a tool to find the frequency response characteristics of such systems with higher complexities.

Although the system can be analyzed accurately by simulation or calculations, misalignment during manufacturing can change the final characteristics of such a system dramatically. Thus, an embodiment of a design needs to consider misalignment to minimize impact of system characteristics.

Figure 22A:
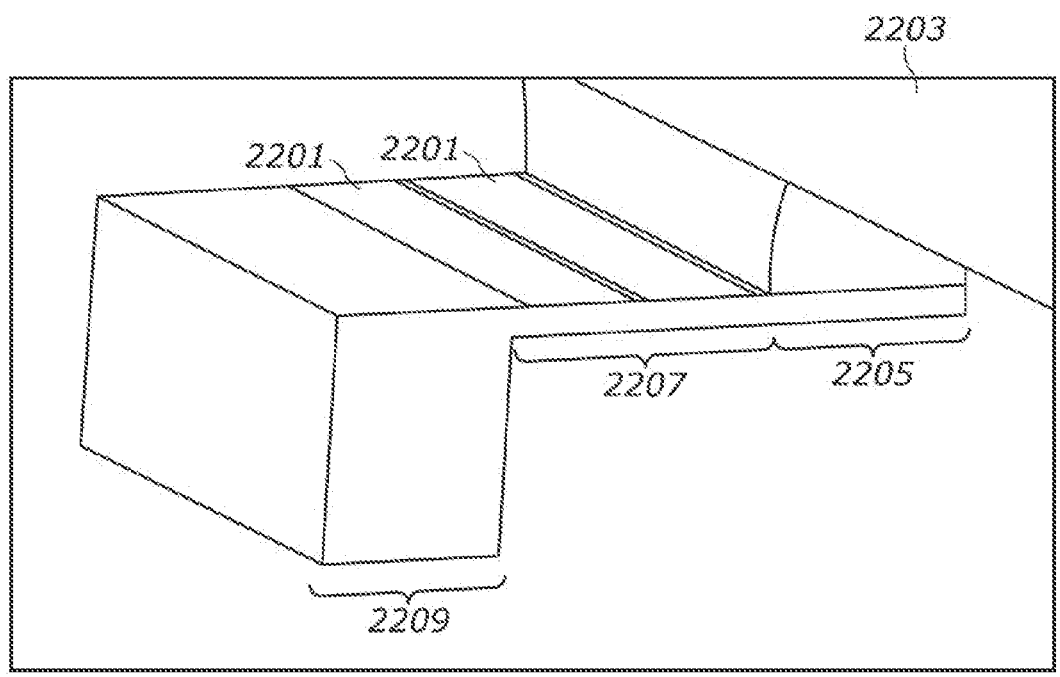
FIG. 22A discloses a first illustrative embodiment of a cantilever.

FIG. 22A discloses a simple design of a cantilever. The cantilever itself may be divided into three sections, a support portion 2205 to the substrate, a suspended cantilever portion 2207, and contact area portion 2205 to the distributed mass load 2203. One or more piezoelectric layer portions 2201 may be located on the cantilever, including the suspended cantilever portion 2207. The piezoelectric layer portions 2201 may be opposite polarity, or driven by phase delay. For example, one piezoelectric layer portion 2201 may be a positive polarity and the other may be a negative polarity. The contact area portion 2205 may be rigid as it is connected to the platform, diaphragm, or membrane. The support area 2209 may be rigid as it is supported to the substrate.

Assuming that the cantilever and the distributed mass are made of two different parts and are assembled together in a separate step, the distributed mass load can be misaligned based on the manufacturing. The misalignment can change the frequency response of the fixed-guided cantilever, thus accuracy may be important of how it is aligned. For example, if the distributed mass load is misaligned to the right, the spring constant will be reduced since the length of the suspended cantilever will be increased.

The resonance frequency of a spring-mass system is:

$$\omega = \sqrt{\frac{k}{m}}$$

Where k is the spring constant and m is the mass.

Therefore, a reduced spring constant will reduce the resonance frequency. Vice versa, if the misalignment is to the left and towards the support substrate, the length of the suspended cantilever will be reduced and therefore an increase in spring constant and resonance frequency will follow. One way to minimize the impact of the misalignment for a cantilever system is to pre-determine the length of the suspended cantilever with a bottom stub, thus mitigating the effects of the suspend portion heavily influencing the frequency.

Figure 22B:
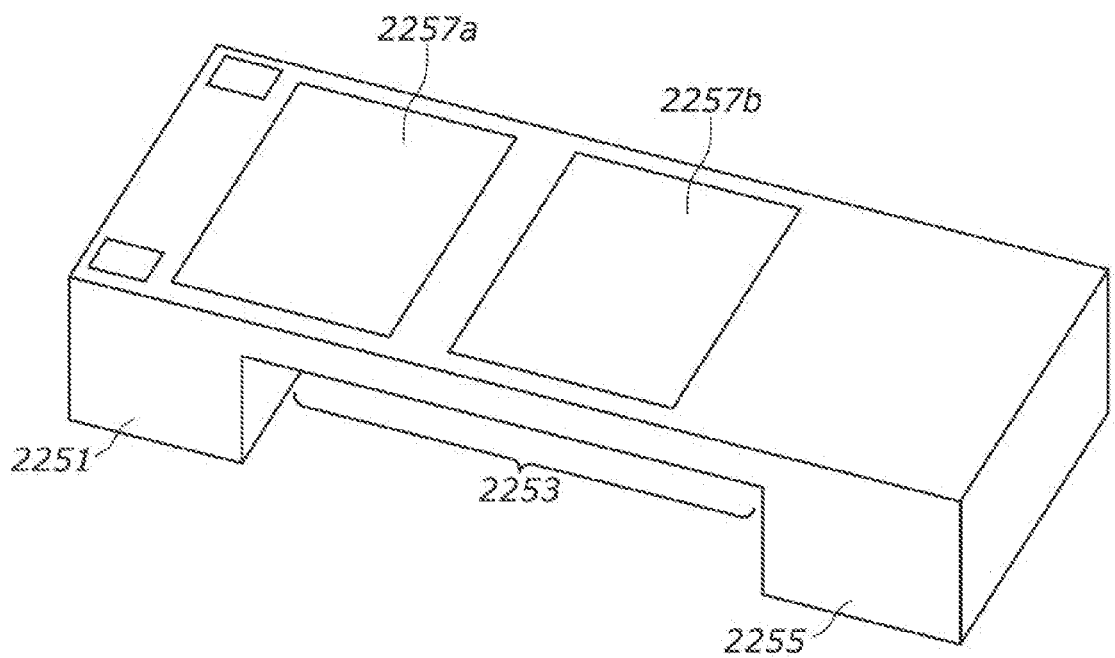
FIG. 22B discloses an example of a cantilever with a bottom stub.

FIG. 22B discloses an example of a cantilever with a bottom stub. The cantilever may include a suspended cantilever portion 2253. The aim of the bottom stub is to determine the portion where it becomes inflexible and therefore to fix the length of the suspended cantilever portion and the spring constant of the cantilever, reducing the influence of the position of the distributed mass load. The substrate may include a left portion 2251 for support and a right portion 2255 for support. The cantilever may include a piezoelectric layer 2257 with both a positive layer 2257a and a negative layer 2257b. In an alternative embodiment, the piezoelectric layers 2257 may be phase shifted with a 180 degree delayed steering.

Figure 23A:
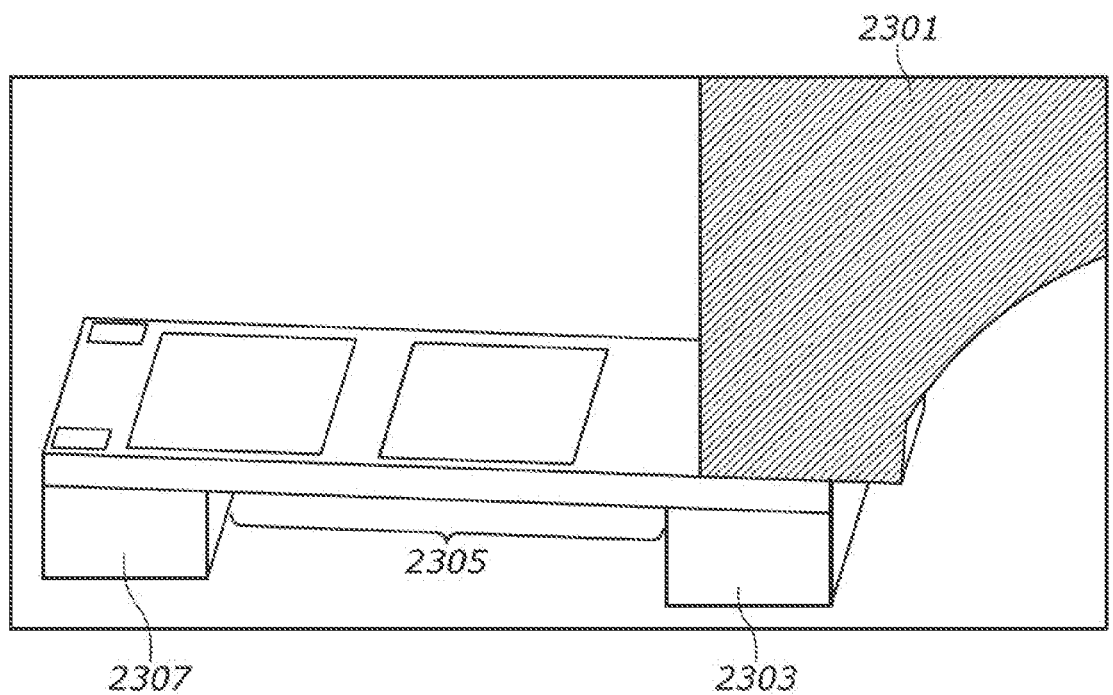
FIG. 23A discloses an example of a misalignment of the distributed mass load.

FIG. 23A discloses an example of a misalignment of the distributed mass load when it is too the right, but the bottom stub limits the change in the length of the suspended cantilever portion and therefore limits the influence on the resonance frequency. As shown in FIG. 23A, the distributed mass load 2301 may be shifting a bit off center from the bottom stub 2303. Thus, that mass load may not sit flush with the stub 2307 and hanging off to the right of the distributed mass load 2305. The substrate (not shown in the figure) may have a hole at the center in one embodiment.

Figure 23B:
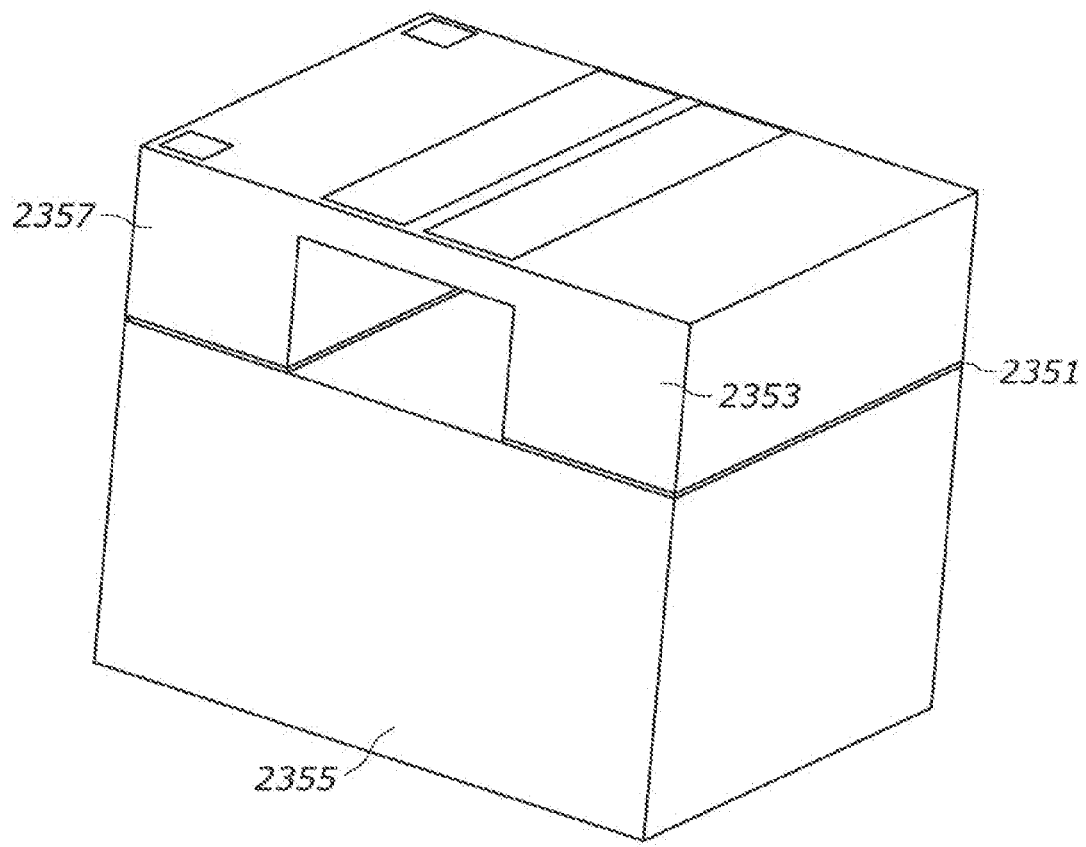
FIG. 23B discloses an example of a cantilever with a bottom stub and a hard stop on the bottom.

FIG. 23B discloses an example of a cantilever with a bottom stub and a hard stop on the bottom. As shown in FIG. 23B, the cantilever may be mounted to a substrate 2355 with a gap 2351 between the substrate, which acts as a hard stop, and the bottom stub. In the event where it would limit the total displacement of the cantilever such that the fracture limit is not exceeded, one can add a hard stop (e.g., the substrate 2355 in this embodiment) on the bottom of the cantilever with the gap determining the allowed maximum displacement. The cantilever may include a fixed connected stub 2357 that does not necessarily include a gap between the substrate and cantilever. In the example of FIG. 23B, the hard stop 2355 may be integrated in the cantilever with a bottom stub. For example, the hard stop could be attached to the cantilever using a wafer bond technique. There may be multiple different ways to implement the hard stop 2355 for the cantilever with a bottom stub 2353.

Figure 24A:
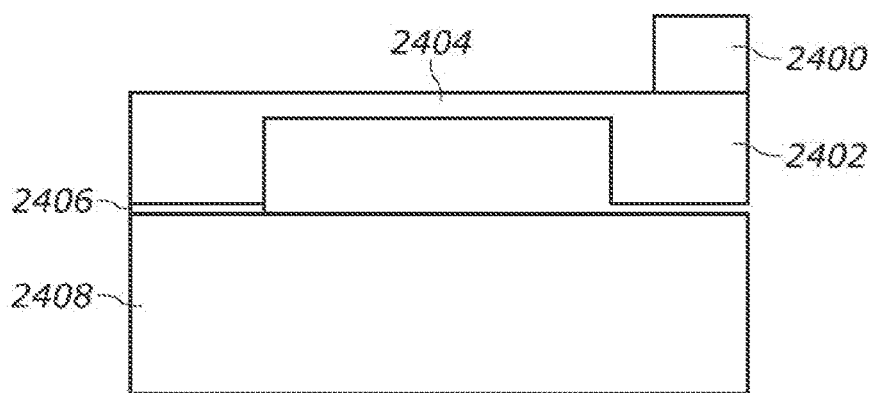
FIG. 24A discloses an embodiment where a gap is determined by a material (e.g. glue, seal glass, etc.) layer connecting to the cantilever.

FIG. 24A discloses an embodiment where a gap is determined by a layer (e.g., glue, seal glass, or another adhesive or material) connecting to the cantilever. The layer 2406 may be typically in the range of 1-10 μm thick, but may be any size of course. The layer 2406 may be added for an increased height. Thus, the more glue utilized at the layer 2406, the more the height. A cantilever 2404 may be utilized that includes a bottom stub 2402. The bottom stub 2402 may not include a layer in some embodiments. A substrate 2408 may include a top surface that the layer 2406 may be located on.

Figure 24B:
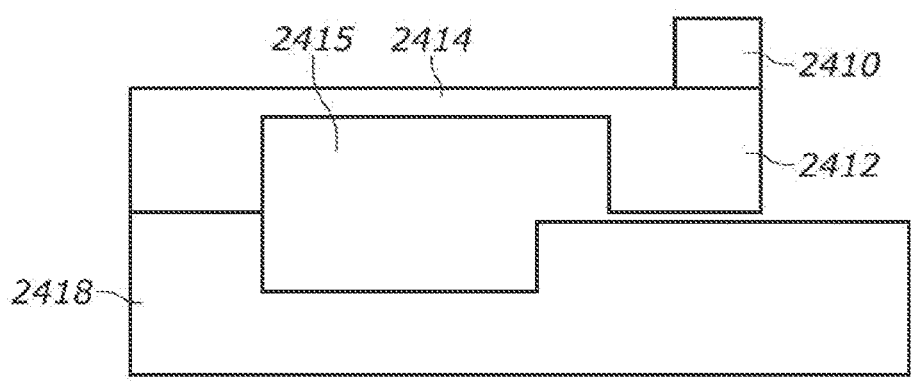
FIG. 24B discloses an embodiment of a cantilever where the gap may be determined by a pre-etched recess on the substrate.

FIG. 24B discloses an embodiment of a cantilever where the gap may be determined by a pre-etched recess on the substrate. In such an embodiment, the substrate height may be slightly reduced at a certain corner below the bottom stub portion 2412 under the distributed mass load 2410. The substrate 2418 may include a cavity 2415 along a top surface of the substrate 2418 and a bottom surface of the cantilever 2414. The distributed mass load 2410 may be located above the bottom stub 2412.

Figure 24C:
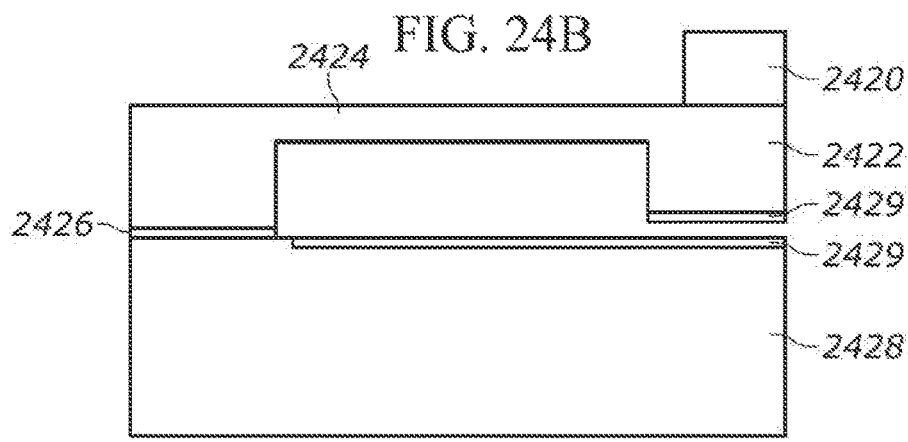
FIG. 24C discloses an embodiment of a cantilever with a distributed mass load with electrostatic actuation.

FIG. 24C discloses an embodiment of a cantilever with a distributed mass load with electrostatic actuation. The distributed mass load 2420 may be located on a top surface of the cantilever 2424. The electrostatic actuator 2429 may be located on a bottom surface of the bottom stub 2422 as well as a top surface of the substrate 2428. There may be a gap between the two electrostatic actuation layers 2429. The substrate 2426 may be a printed circuit board material in one embodiment. The substrate 2428 may be acting both as a support and as a hard stop for the fixed-guided end of the cantilever.

Figure 24D:
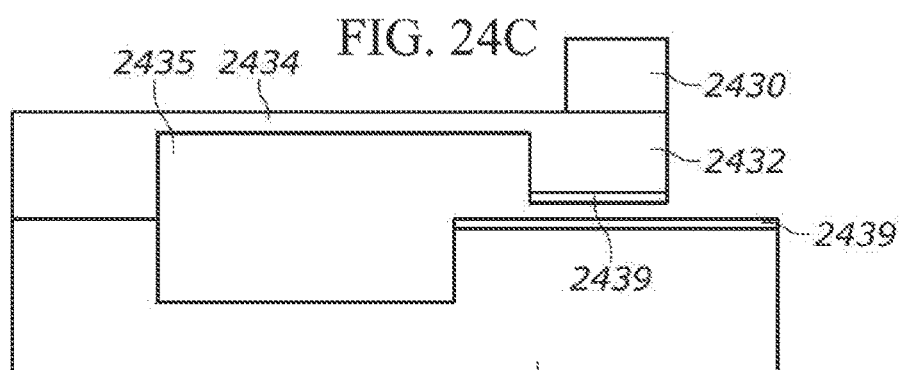
FIG. 24D discloses an embodiment of a cantilever with a distributed mass load with electrostatic actuation with a cavity.

FIG. 24D discloses an embodiment of a cantilever with a distributed mass load 2430 with electrostatic actuation with a cavity 2435. The cavity 2435 may be an optional cavity. The distributed mass load 2430 may be located on a top surface 2434 of the cantilever 2438. The electrostatic actuator 2439 may be located on a bottom surface of the bottom stub 2432 as well as a top surface of the substrate 2438. The substrate may be a printed circuit board material in one embodiment. The substrate 2438 may be acting both as a support and as a hard stop for the fixed-guided end of the cantilever.

Figure 25A:
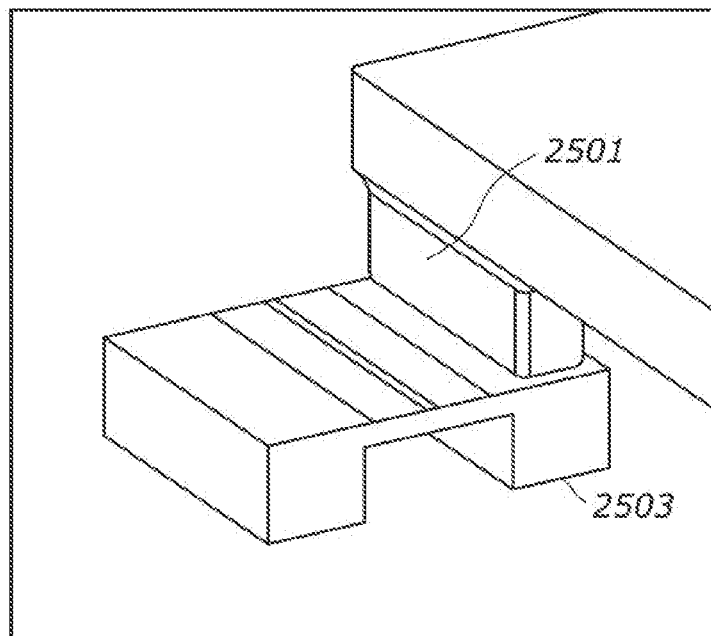
FIG. 25A discloses a cantilever with near-perfect to perfect alignment.

FIG. 25A discloses a cantilever with perfect alignment. As shown, the feet 2501 are aligned to be matched up in a center of the bottom stub 2503. In such an embodiment, the distributed mass load is centered and where the contact surface of the feet is smaller than the area of the bottom stub and is perfectly aligned at the center.

Figure 25B:
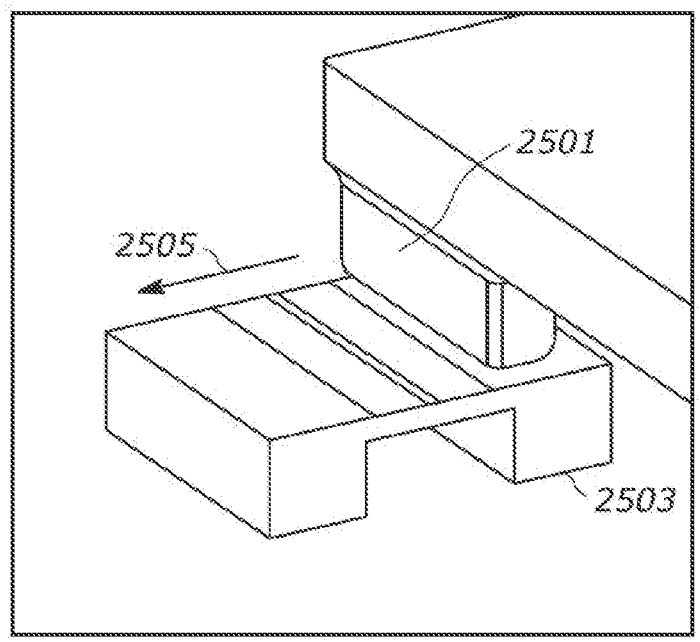
FIG. 25B discloses a cantilever with offset alignment.

FIG. 25B discloses a cantilever with offset alignment. As shown, the feet 2501 are moved forward 2505 and closer to the piezoelectric layers. The feet 2501 may be integral to the membrane or a separate piece of material that extends away from the bottom surface of the membrane and attached to a top surface of the cantilever. In such an embodiment, the misalignment may mitigate any change in resonance due to the stub 2503. In such an embodiment, the stub 2503 is a bottom stub extending away from the surface of the cantilever. As such, the misalignment can be minimized if the area of the feet of the platform (e.g., diaphragm and membrane) are designed to be smaller than the area of the bottom stub on the cantilever. Thus, the smaller area of the feet 2501 may allow for misalignment with minimal influence on the spring constant of the cantilever.

Figure 26A:
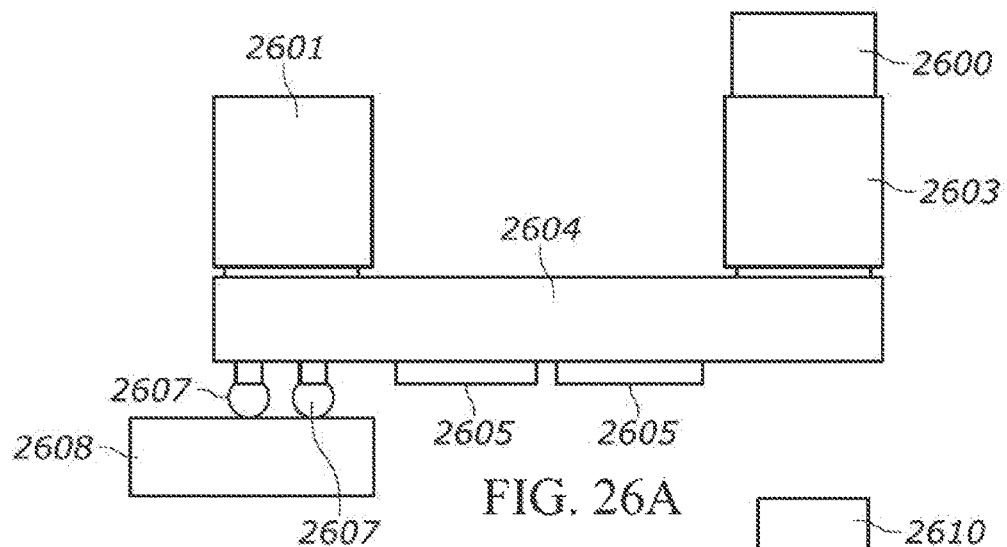
FIGS. 26A-26D discloses various embodiments of a cantilever with top stub designs.

FIG. 26A is an example of a cantilever design utilizing a top stub design. In essence, the cantilever 2604 may be flipped upside down but still provides a similar design that mitigates influences of misalignment. In such an example, the cantilever 2604 has a top support 2601 and a top stub 2603. The top stub 2603 may be connected to the distributed mass load 2600 (e.g., the membrane, foot, etc.). In another embodiment, the piezoelectric layer 2605 may also be on a bottom surface of the cantilever 2604. The piezoelectric layer 2605 may be different polarities for each layer. The substrate 2608 may be connected to the cantilever 2604 via flip chip bonding 2607. The flip chip bonding 2607 may provide an electrical connection to the substrate 2608.

Figure 26B:
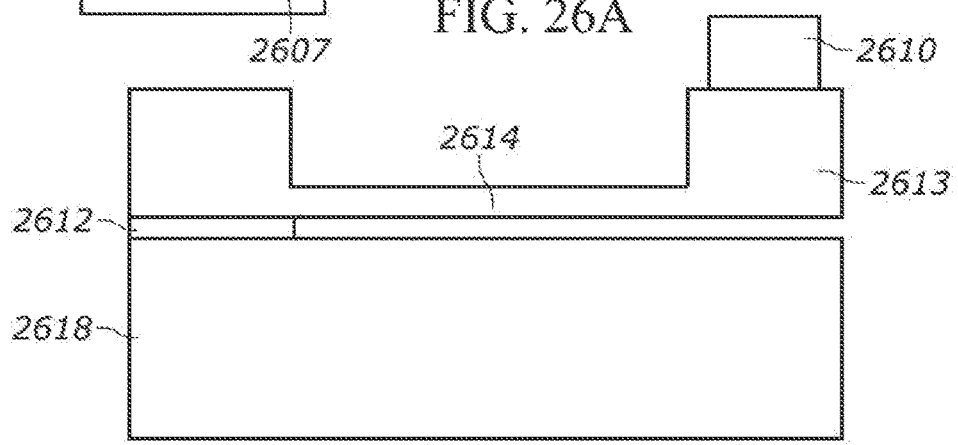

FIG. 26B is an example of a cantilever and substrate utilizing a top stub design with a material layer, which may include glue or any other layer. The substrate 2618 may be acting as both a support and as a hard stop for the fixed-guided end of the cantilever 2614. The cantilever 2614 may be attached to the substrate 2618 via a glue layer 2612. The glue layer 2612 may be utilized to increase the height of the cantilever 2614 and to create the gap between the cantilever 2614 and the substrate 2618. The top stub 2613 may extend away from a top layer surface of the cantilever 2614. The top stub 2613 may attach to the distributed mass load 2610, which may be the membrane, foot, or other portion of a distributed mass load.

Figure 26C:
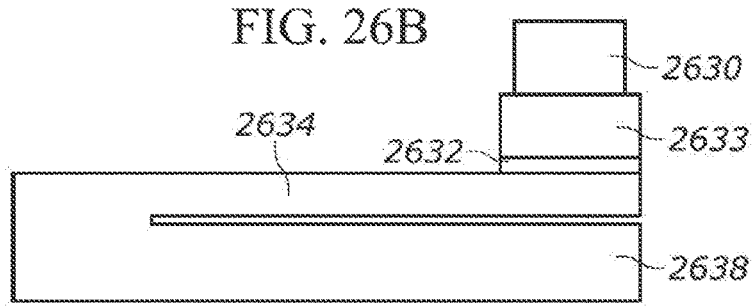

FIG. 26C is another example of a top stub cantilever for a silicon substrate design. In such an embodiment, a silicon substrate 2638 may be utilized instead of a PCB. In such an embodiment, the silicon substrate 2638 may have a cantilever 2634 design integral to the silicon substrate 2638. A gap may exist from a bottom surface of the cantilever portion 2634 and a top surface of the silicon substrate 2638 portion. The top stub portion 2633 may be a separate portion. The top stub portion 2633 may be connected to the cantilever portion 2634 via a wafer bond 2632. The wafer bonding process 2632 may be utilized for an accurate manufacturing.

Figure 26D:
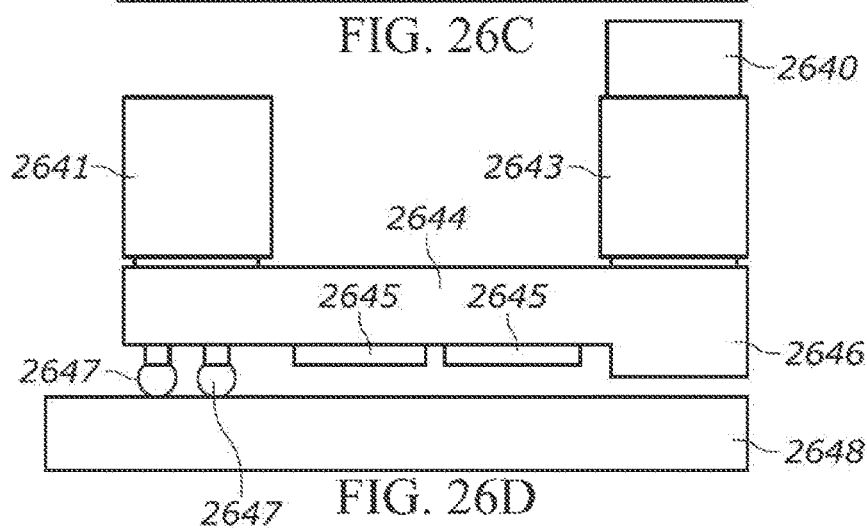

FIG. 26D is yet another embodiment of a top stub design that also includes an extra bottom stub(s). In such an embodiment, the cantilever 2644 may include both a top stub 2643 connected to the distributed mass load 2640 and a bottom stub 2646. The top stub 2643 and bottom stub 2646 may include a similar surface area in an embodiment. In yet another embodiment, the bottom stub 2646 may be shorter. A surface of the bottom stub 2646 may be adjacent a top surface of the substrate 2648. A top support portion 2641 may also be attached to the cantilever 2644. The piezoelectric layer 2645 may be located on a bottom surface of the cantilever 2644 in one embodiment. In another embodiment, the piezoelectric layer 2645 may also be on a top surface of the cantilever 2644. The piezoelectric layer 2645 may be different polarities for each layer. The cantilever 2644 may be attached to the substrate 2648 via flip chop bonding 2647 for an electrical connection.

Figure 27A:
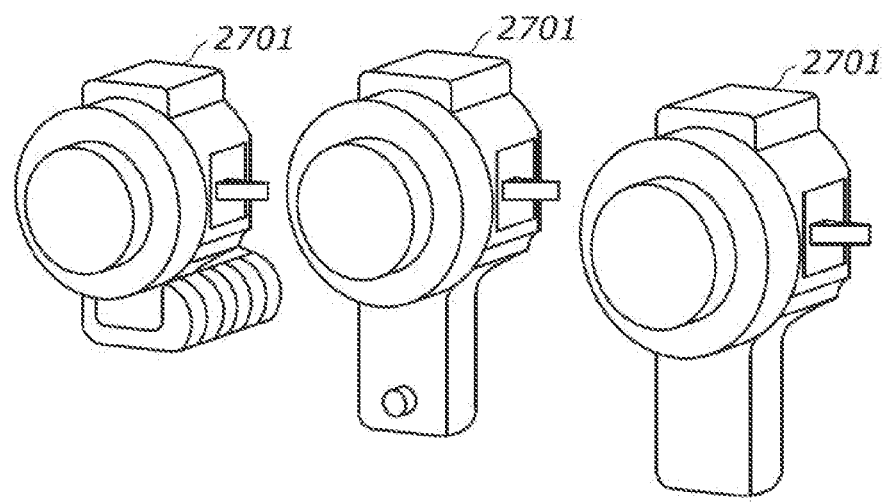
FIG. 27A discloses an embodiment of a parking-assist sensor.
Figure 27B:
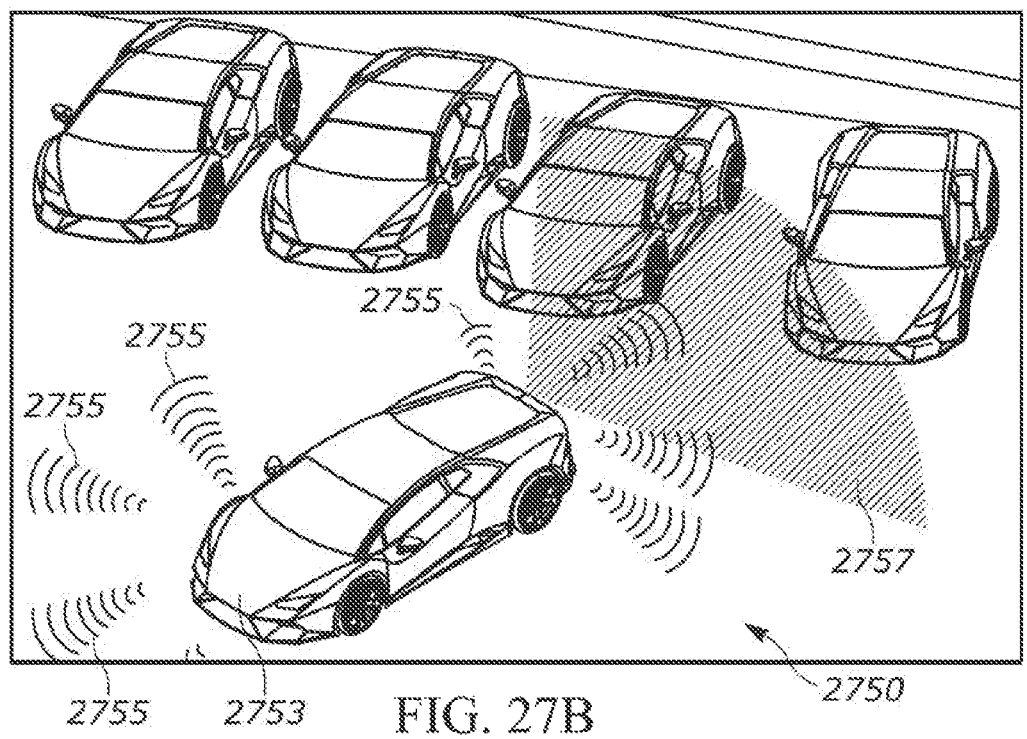
FIG. 27B discloses an illustration of the parking-assist sensor in operation.

FIG. 27A shows the individual sensors of a parking assist system. FIG. 27B illustrates an embodiment of an operation of a typical parking-assist system. The size and interface of the sensors may be typically standard across all manufacturers. The standard size also defines the opening in the bumper for the sensor membrane. As shown, the sensors 2701 may include various shapes of housings. One or more transducer elements may be utilized and contained within the housings of the sensors 2701.

At 2750, an illustration of a vehicle 2753 utilizing the parking assist system. The sensors of the vehicle may emit a transmit signal 2755 to determine objects proximate the vehicle 2753. Signal 2757 shows the full coverage of the transmit signals 2755 on the rear side of the vehicle 2753. Objects will reflect the signals and the sensors in the vehicle 2753 will receive, allowing to identify one or more vehicles proximate the main vehicle 2753

There are a number of factors, which may determine the cost and performance of an ultrasound parking assist system. Among those are the maximum and minimum range at which it can detect objects and the field of view (FoV) it covers. Optimizing those parameters involves certain tradeoffs. Opening a wider field of view in the vertical direction allows for the detection of obstacles at a higher elevation, for example a half-open garage door, as well as obstacles on the ground, close to the vehicle, such as curbs and fallen objects. On the other hand, a wider vertical field of view also causes more ground reflections, which are unwanted in the system, especially when targets at a longer distance are of interest. A wider FoV in the horizontal direction also improves the spatial coverage, however it leads to the simultaneous detection of multiple targets, which places a higher burden on the digital processing back-end. Ideally, we would like to be able to focus on small areas of interest, while at the same time having the opportunity to cover the entire space around the vehicle. This would be possible with a phased array system, which uses a scanning narrow beam to build a spatial image. The cost and size of such a system would be prohibitive for mass adoption in the short term. As a compromise, we propose a device, which enhances the functionality in certain important aspects, without achieving the full performance of a phased array.

Figure 28:
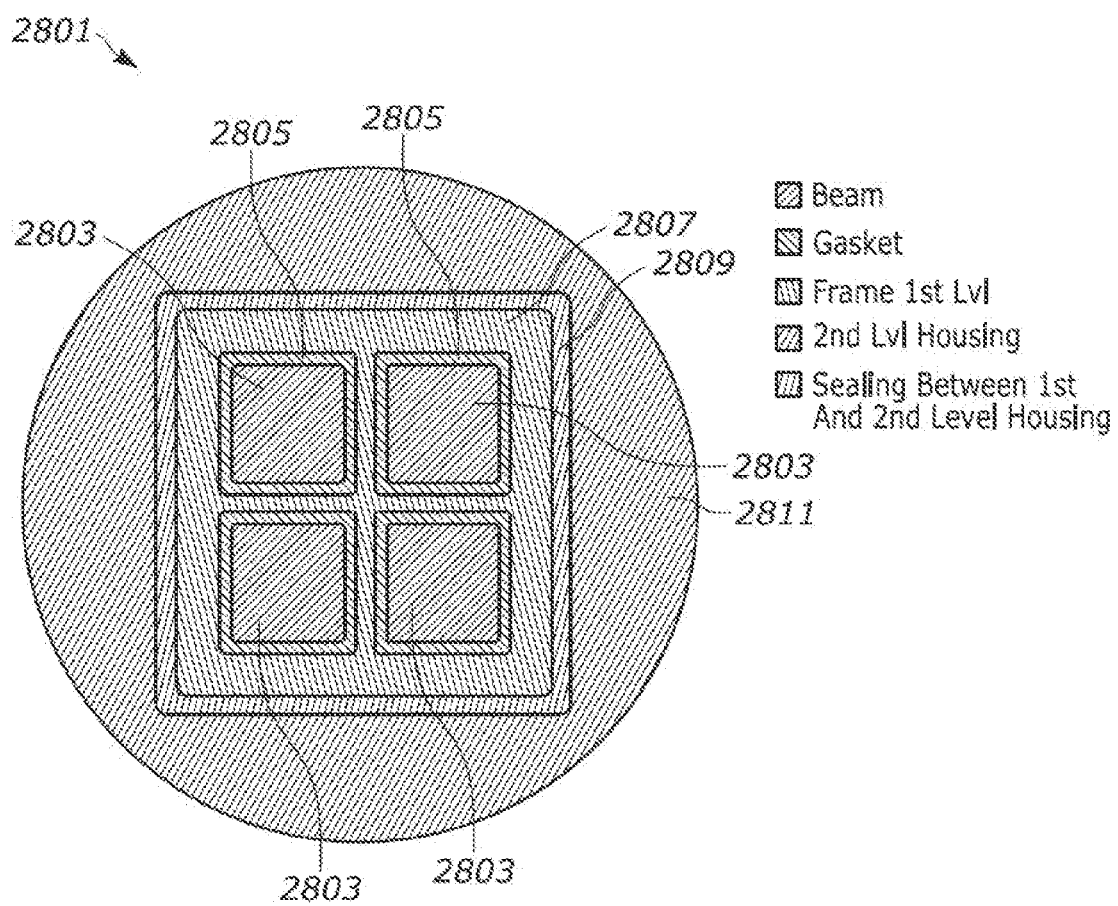
FIG. 28 discloses a top-view of a sensor element with an array of transducers with square transducer elements.

FIG. 28 discloses a top-view of an embodiment of configuration of an array of transducers 2801. As a first step, we consider two modes of operation-one for imaging objects at a larger distance with a narrower FOV and a second one for closer objects, with a wide FoV. The principles of wave radiation show that the field of view is directly proportional to the wavelength and inversely proportional to the size of the radiating element. Therefore, an adaptive FoV would require adaptive size of the radiating (and receiving) transducer surface. To achieve this, we propose to split the transducer membrane into individually controlled sections. Each section may be an independent transducer or beam 2803. It may include four rectangular elements 2803 with membranes moving out of plane in a piston-like manner. The transducer elements may have a center point half a wavelength apart from each other. A gasket 2805 seals off the perimeter of each element against moisture and contamination. The device may fits within the membrane area of a standard ultrasound sensor 2801, but it would also be possible to reduce the size of a sensor to the frame of the array 2807. Even though we use four elements as an example, the device can use other configurations as well that include any number of elements 2803. The sealing 2809 may? between the frame of the array 2807 and a sensor housing 2811 may be utilized to further protect and secure the elements from harsh environments, but it would be also possible to combine the frame of the housing with the sensor housing as one element without having a sealing 2809.

Figures 29A, 29B, 29C, 29D:
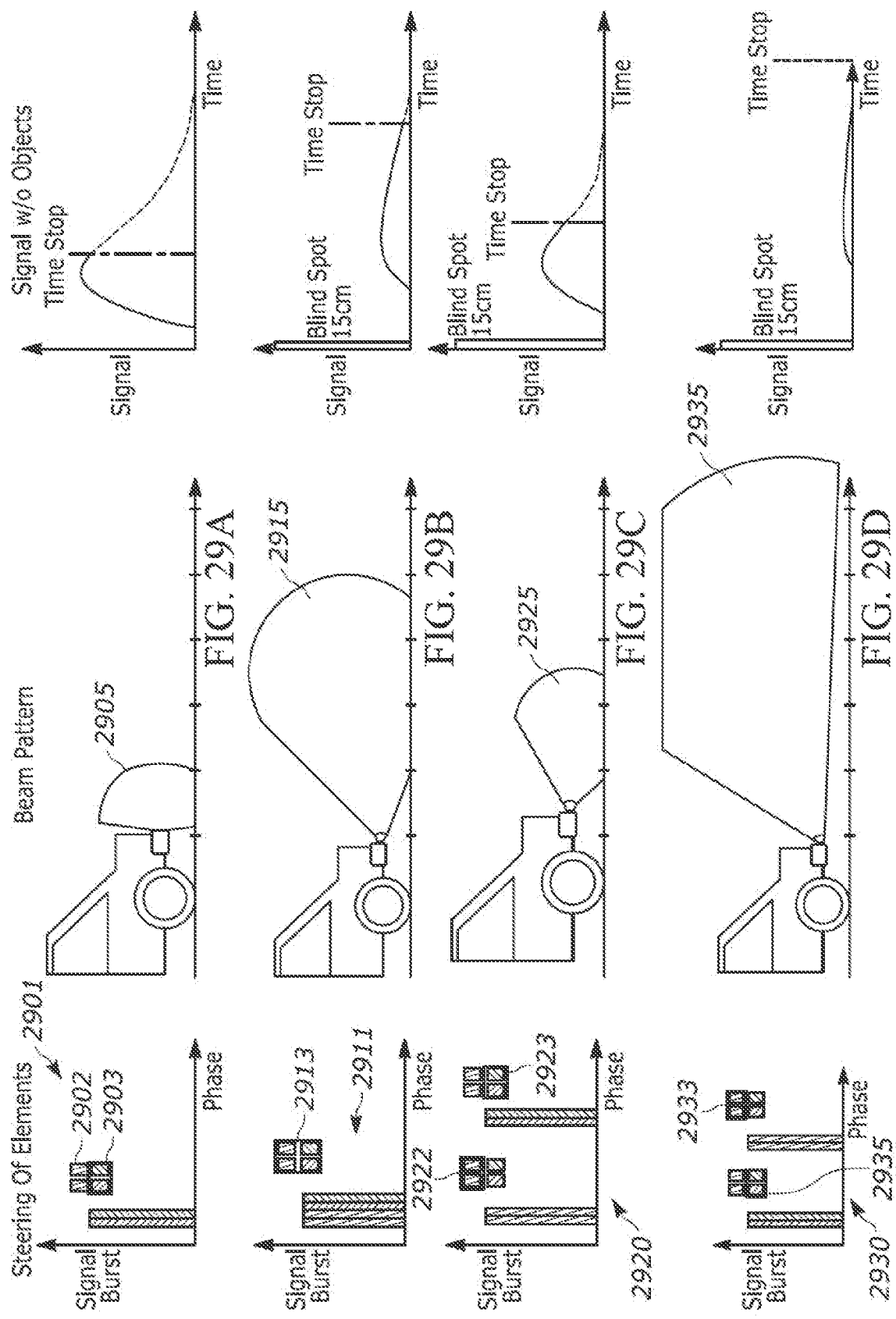
FIG. 29A discloses an embodiment utilizing one row of elements to transmit and the other row of elements to receive, and accompanying illustrations and graphs.
FIG. 29B discloses an embodiment showing a mode of operation, where all elements are configured to operate synchronously for both transmitting and receiving, resulting in similar performance as standard parking-assists systems, and accompanying illustrations and graphs.
FIG. 29C discloses an embodiment of one or more transducer elements, running with phase shift steering, resulting that the FoV is directed downwards for short range detection, and accompanying illustrations and graphs.
FIG. 29D discloses an embodiment of one or more transducer elements, running with phase shift-steering, resulting that the FoV is directed upwards for long range detection, and accompanying illustrations and graphs.

FIG. 29A discloses graphs and beam patterns associated with an embodiment activating a lower row of transducer elements. FIG. 29B discloses graphs and beam patterns associated with an embodiment activating both a top and bottom row of transducer elements. FIG. 29C discloses graphs and beam patterns associated with an embodiment activating top row of transducer elements followed by a lower row of transducer elements. FIG. 29D discloses graphs and beam patterns associated with an embodiment activating bottom row of transducer elements followed by a top row of transducer elements. In FIG. 29A, one row of elements may be used to transmit and the other to receive the signal. In such an embodiment, the lower row 2903 may be activated. This results in a field of view of nearly +/−90 degrees, which may allow the detection of close-in objects on the ground. The transmitted power in this case is half of the total available and therefore the maximum range is lower. Furthermore, since different elements are used for transmit and receive, there is no need to introduce a dead time for membrane ring-down and the sensor can detect objects at a closer minimum range compared to the standard operation. Nevertheless after the ring down of the transmit elements could also be used to receive signals allowing a time of flight measurement and due to this a height measurement of the received signal. At 2901, the system may indicate that the lower transducer elements 2903 may be activated to provide a signal, while the top transducer elements 2902 are not activated. The beam pattern 2905 may indicate a short range, but a wide field of view. In such a scenario, it may be useful for the vehicle and driver to look at the ground.

FIG. 29B shows the standard mode of operation, in which all elements operate synchronously and are used for both transmit and receive. This may be similar to the operation of most sensor functions. It provides maximum signal power at beam pattern 2915 and the long range for detecting far away objects of interest. Due to the multiplexing of the transducers between transmit and receive, there may be a dead time and the minimum detectable range that is higher than in FIG. 29A. Also, the larger effective aperture of the radiating surface reduces the field of view by approximately half. This may reduce ground reflections and further improve the signal quality for faraway objects. Close-in objects on the ground may not be detected, however. Thus, all the transducer elements 2913 may be activated and the transducer elements may be transmitting and receiving synchronously at 2911 allowing also height measurements of objects the receiving signals by time of flight evaluation.

FIG. 29C shows an illustration of a beam pattern steering downwards at a short range. The top half of transducer elements 2922 may be actuated first and out of sync with the bottom half of transducer elements 2923, as shown in graph 2920. Thus, the beam pattern 2925 may be tilted down in order to interrogate the ground because of various obstacles.

Thus, the elements are stationary, but the phase difference between the signal is applied to different elements tilts the beam. In such an embodiment, the top row of elements 2922 and the bottom row 2923 of elements (e.g., there is only one beam formed by the elements) may be actuated out of phase. Thus, beam pattern 2925 emitting from the vehicle may steer towards the ground and obstacles at the lower portion of the vehicle that are closer to the ground.

FIG. 29D shows an example illustration of a beam pattern steering upwards at a long range. The long range may thus send a signal at a distance of at least 5 meters. In such an embodiment, the bottom row of elements 2935 may be activated first to transmit, followed by the top row of elements 2933. In such an embodiment, the beam pattern 2935 may be steered upwards to avoid ground reflection finally allowing to indicate obstacles at far distances with less unwanted input by the ground reflection. As shown, the row of elements may be actuated out of phase based on the graph of 2930.

Figure 30:
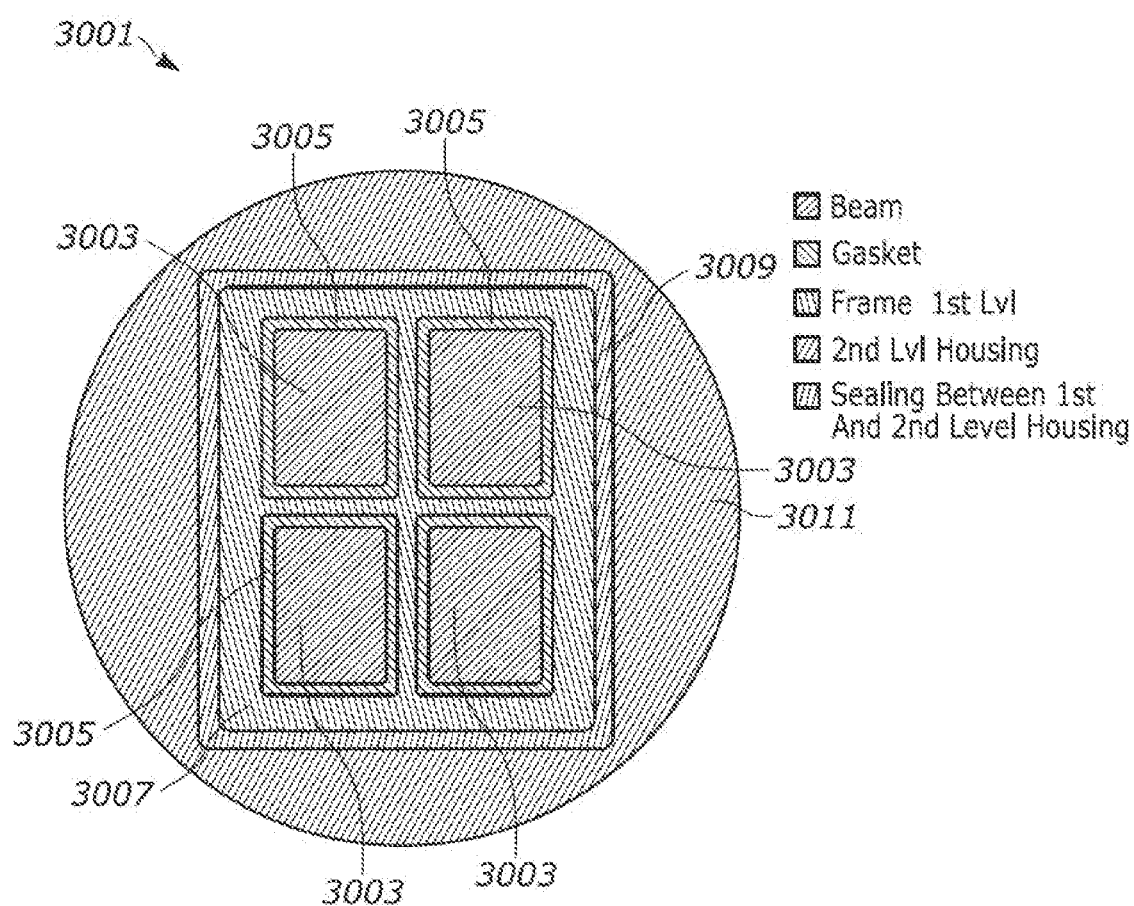
FIG. 30 discloses a sensor element configuration disclosed to include rectangular beams.

In FIG. 30 a transducer element may be shown with rectangular beams. The transducer element 3003 may be square or rectangular in shape, as well as any other shape (e.g., circular). The transducer element 3003 may be a 2.6 mm wide and 2.6 mm in length. A gasket 3005 seals the perimeter of each element against moisture and contamination. The outer frame 3007 (e.g., first level frame) may have a width of 1.0 mm and inner frame width of 0.4 mm In FIG. 30, as opposed to the configuration in FIG. 28, the transducer element may be rectangular in shape with a transducer element being 3.4 mm by 2.6 mm. This may make the first level frame 3007 to be taller in height (e.g., 10.4 mm versus 8.8 mm). The seal 3009 may thus be larger and rectangular in shape. The sealing 3009 may be between the first level housing 3007 and a second level housing 3011 may be utilized to further protect and secure the elements from harsh environments.

The dimensional aspect may be important, since a typical circular sensor array 3001 may have an outer diameter of 15.5 mm. This may be utilized for the outer housing. Finally, the sizing of the transducers may be as such that it also allows the sensor to operate as a phased array and provide a certain degree of directivity. In particular, the elements may be spaced apart by half wavelength (approximately 0.7*lambda<space<1.4*lambda) to avoid grating lobes. This may be a condition for phased arrays. A phased array of two elements provides very limited beam steering capability, on the order of +/−20 degrees. Nevertheless, this may be sufficient to tilt the beam upwards in the vertical direction when imaging faraway targets and thus to reduce the influence of ground reflections. Conversely, it can also be tilted down and allow for imaging close-in targets on the ground. For example, FIGS. 29C and 29D show the two modes. They can provide additional information and improve the imaging capability. Similarly, beam steering can be achieved in the horizontal direction. The power of the transmitted signal can also be varied for different ranges of interest.

The embodiment disclosed in the array 3001 of FIG. 30 discloses a sensor element configuration utilized to obtain different horizontal and vertical field of views. Some applications might require the sensor to have a mode of operation, which exactly matches the field of view of for instant current sensors. In this case, the individual elements need to be sized to provide the same equivalent aperture as the original sensor, when operated synchronously. Depending on the specified FoV, this might violate the half-wavelength requirement and will limit the beam steering capability. This tradeoff should be taken into account. In such a configuration, the sensor may be required to have a narrower vertical field of view. This configuration of the device can still offer horizontal beam steering, however in the vertical direction the steering range will be limited by the appearance of grating lobes, since the elements are spaced apart by more than half wavelength.

Figure 31A:
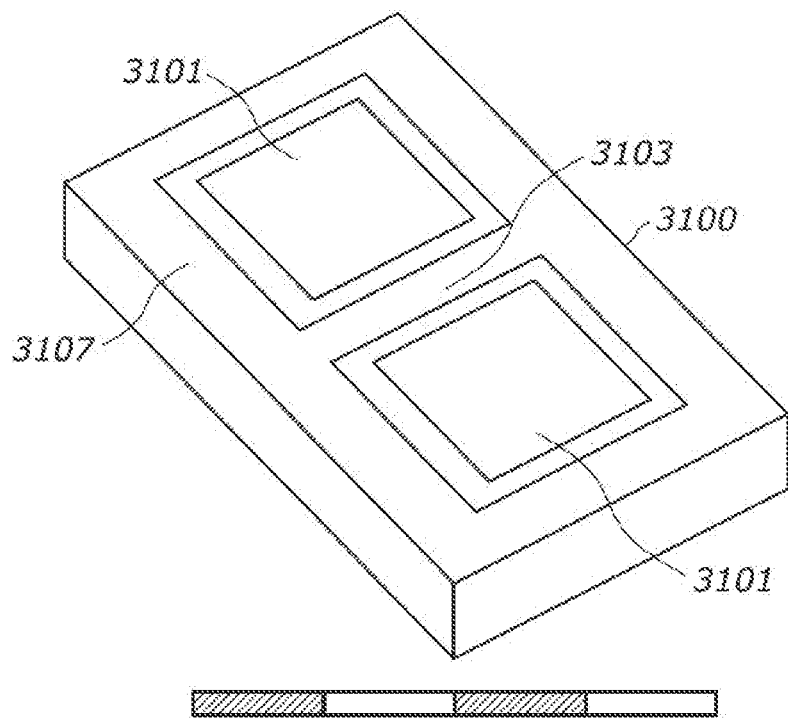
FIG. 31A discloses an embodiment of an array including a frame with two transducer elements.
Figure 31B:
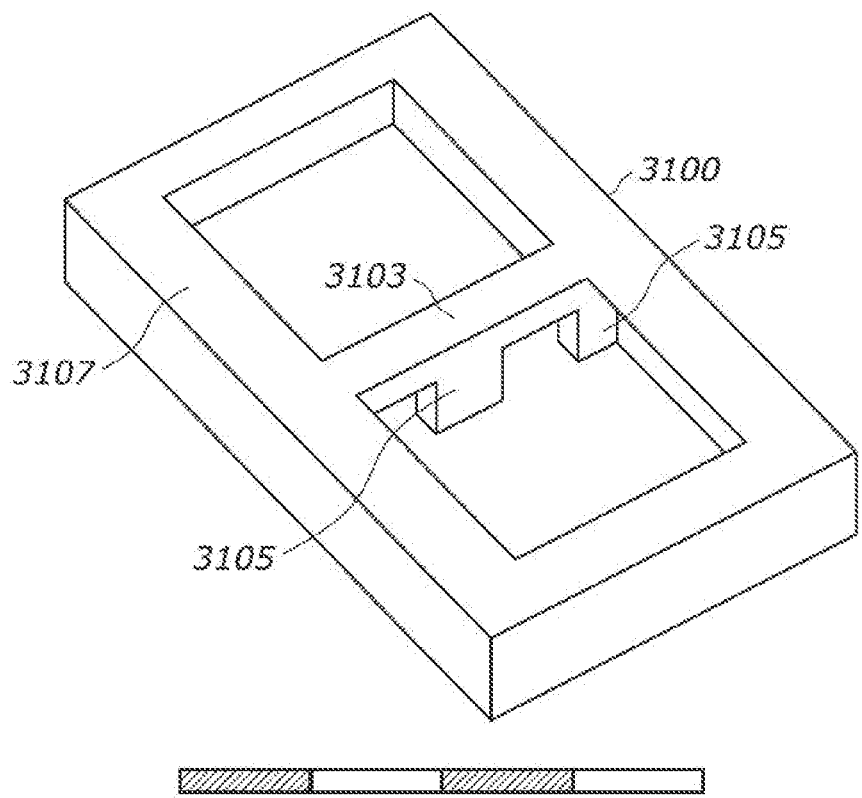
FIG. 31B discloses a frame associated with the array of two elements, showing the transducer elements missing.

FIGS. 31A and 31B shows an illustrative example of an array of two elements. FIG. 31A, for example, shows two sensor elements 3101 within a frame 3100. For proper operation, minimal cross coupling between the elements may be required. For example, when one element is actuated, it should not affect or vibrate the surrounding elements. The frame may ensure to mitigate the vibration or affect. The frame material may be extended from a cross section portion in one embodiment. Thus, one way to ensure that is to have the frame material between the elements extended and mounted to the bottom substrate, as shown in FIG. 31B. In an embodiment with four transducer elements, the frame material may extend away from both a vertical midsection 3105 and a horizontal mid section 3103, which are shown in FIG. 30. Thus, the vertical midsection 3105 may separate the transducer elements 3101 and mitigate vibration by extending away from a top surface 3107 of the frame 3100 and towards a bottom surface (not shown). While there may be a gap between the vertical midsections 3105 in FIG. 31B, that portion may be filled in other embodiments.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, case of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. An ultrasound transducer of a vehicle system, comprising:
a support member that attaches to and connects to the bottom portion of a membrane of the ultrasound transducer and supports the membrane, wherein the support member includes one or more cantilevers with a first end attaching to the membrane and a second end attaching to a support portion of the support member that attaches to the substrate, wherein the one or more cantilevers extend across and floats above the substrate, wherein the first end of one of the cantilevers includes a stub extending away from a surface of the cantilever, wherein the stub extends away from the surface without contacting the substrate, wherein the one or more cantilevers includes one or more piezoelectric portions on the surface of the cantilever.

2. The ultrasound transducer of claim 1, wherein the surface is a bottom surface of the cantilever.

3. The ultrasound transducer of claim 1, wherein the surface is a top surface of the cantilever.

4. The ultrasound transducer of claim 1, wherein the one or more cantilevers include a suspended cantilever portion between the stub and the support portion, wherein the suspended cantilever portion includes the one or more piezoelectric portions.

5. The ultrasound transducer of claim 1, wherein the stub includes a width wider than feet associated with the membrane, wherein the feet associated with the membrane are in contact with the stub.

6. The ultrasound transducer of claim 1, wherein a gap is formed between a top surface of the substrate and a bottom surface of the stub, wherein the substrate is configured as a hard-stop in response to vibration of the cantilever.

7. The ultrasound transducer of claim 1, wherein the support portion is attached to the substrate via a glue layer.

8. The ultrasound transducer of claim 1, wherein a cavity is formed by surfaces associated with the cantilever, the stub, and the substrate.

9. The ultrasound transducer of claim 1, wherein the substrate is a printed circuit board (PCB).

10. The ultrasound transducer of claim 1, wherein the stub includes an electrostatic actuation layer configured to vibrate the cantilever in response to electrostatic force being applied.

11. An ultrasound transducer of a vehicle system, comprising:
a membrane configured to vibrate to generate an ultrasound when voltage is applied and further configured to vibrate in an out-of-plane movement; and
a support member that attaches to and connects to the bottom portion of a membrane of the ultrasound transducer and supports the membrane, wherein the support member includes one or more platforms with a first end attaching to the membrane and a second end attaching to a support portion of the support member that attaches to the substrate, wherein the platform extends across and floats above the substrate, wherein the first end of the platform includes one or more stubs extending away from a surface of the platform, wherein the one or more stubs extend away from the surface without contacting the substrate, wherein the one or more platforms includes one or more piezoelectric layers on the surface of the platform.

12. The ultrasound transducer of claim 11, wherein a width associated with the stub is greater than a width associated with a foot of the membrane, wherein the foot of the membrane is connected to the platform.

13. The ultrasound transducer of claim 11, wherein the one or more stubs includes a top stub extending away from a top surface of the platform facing the membrane and a bottom stub extending away form a bottom surface of the platform facing the substrate.

* * * * *